(12) United States Patent
Nair

(10) Patent No.: US 11,766,467 B2
(45) Date of Patent: Sep. 26, 2023

(54) METHODS OF TREATING WOUNDS USING CATHEPSIN K INHIBITORS

(71) Applicant: University of Wyoming, Laramie, WY (US)

(72) Inventor: Sreejayan Nair, Laramie, WY (US)

(73) Assignee: University of Wyoming, Laramie, WY (US)

( * ) Notice: Subject to any disclaimer, the term of this patent is extended or adjusted under 35 U.S.C. 154(b) by 283 days.

(21) Appl. No.: 17/006,003

(22) Filed: Aug. 28, 2020

(65) Prior Publication Data

US 2020/0390848 A1 Dec. 17, 2020

Related U.S. Application Data

(63) Continuation-in-part of application No. 16/121,443, filed on Sep. 4, 2018, now Pat. No. 10,758,559.

(60) Provisional application No. 62/894,679, filed on Aug. 30, 2019, provisional application No. 62/553,702, filed on Sep. 1, 2017.

(51) Int. Cl.
| | |
|---|---|
| *A61K 38/08* | (2019.01) |
| *A61P 17/02* | (2006.01) |
| *A61K 31/165* | (2006.01) |
| *C12N 15/113* | (2010.01) |
| *A61L 15/44* | (2006.01) |
| *A61L 15/42* | (2006.01) |
| *A61K 38/48* | (2006.01) |

(52) U.S. Cl.
CPC ............ *A61K 38/08* (2013.01); *A61K 31/165* (2013.01); *A61K 38/4886* (2013.01); *A61L 15/425* (2013.01); *A61L 15/44* (2013.01); *A61P 17/02* (2018.01); *C12N 15/1137* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 5,457,093 | A | 10/1995 | Cini et al. |
| 9,833,498 | B2 | 12/2017 | Keller et al. |
| 9,873,668 | B2 | 1/2018 | Chaplin et al. |
| 9,943,522 | B2 | 4/2018 | Golz et al. |
| 10,005,823 | B2 | 6/2018 | Lin et al. |
| 10,034,826 | B2 | 7/2018 | Idkowiak-Baldys et al. |
| 10,045,950 | B2 | 8/2018 | Tsai et al. |
| 10,058,633 | B2 | 8/2018 | Ferrari et al. |
| 10,758,559 | B1 | 9/2020 | Nair |
| 2003/0003157 | A1 | 1/2003 | Ohan et al. |
| 2006/0111440 | A1 | 5/2006 | Gauthier et al. |
| 2006/0275366 | A1* | 12/2006 | Malcolm ............ A61K 31/4709 514/1.3 |
| 2007/0258952 | A1 | 11/2007 | Tong et al. |
| 2008/0125442 | A1 | 5/2008 | Percival |
| 2008/0138277 | A1 | 6/2008 | Epstein et al. |
| 2009/0111771 | A1 | 4/2009 | Cullis-Hill et al. |
| 2013/0217766 | A1* | 8/2013 | Fan ........................ A61P 19/10 514/521 |
| 2014/0271609 | A1 | 9/2014 | Keller et al. |
| 2015/0352064 | A1 | 12/2015 | Bitar et al. |
| 2016/0186259 | A1 | 6/2016 | Ofir et al. |

FOREIGN PATENT DOCUMENTS

WO WO-2016042131 A1 * 3/2016 ............. A61K 31/10

OTHER PUBLICATIONS

Odanacatib Merck CAS registry No. 603139-19-1 1 page, retrieved online on Mar. 13, 2023 (Year: 2023).*
Sharma et al., "Structural requirements for the collagenase and elastase activity of cathepsin K and its selective inhibition by an exosite inhibitor", Biochem. J., vol. 465, pp. 163-173, 2015.
Clark et al., "Tissue Engineering for Cutaneous Wounds", Journal of Investigative Dermatology, vol. 127, issue 5, pp. 1018-1029, 2007.
Runger et al., "Role of Cathepsin K in the Turnover of the Dermal Extracellular Matrix during Scar Formation", Journal of Investigative Dermatology, vol. 127, pp. 293-297, 2007.
Bromme et al., "Cathepsin K inhibitors for osteoporosis and potential off-target effects", Expert Opin Investig Drugs vol. 18(5), pp. 585-600, May 2009.
Hirai et al., "Cathepsin K Is Involved in Development of Psoriasis-like Skin Lesions through TLR-Dependent Th17 Activation", J Immunol 2013; vol. 190, pp. 4805-4811, Prepublished online Mar. 29, 2013.
McCarty et al., "Proteases and Delayed Wound Healing, Advances in Wound Care", vol. 2, No. 8, pp. 438-447, Oct. 2013.
Gao, et al., "Acceleration of diabetic wound healing using a novel protease-anti-protease combination therapy", Proc. Natl. Acad. Sci., vol. 112(49) pp. 15226-15231, Dec. 2015.
Han et al., "Chronic Wound Healing: A Review of Current Management and Treatments", Adv. Ther. vol. 34, pp. 599-610, Jan. 2017.
Nair, et al., "Targeting Cathepsin K to Promoted Diabetic Wound Healing", The FASEB Journal vol. 31 No. 1 Supplement 673.11, Apr. 2017.

(Continued)

*Primary Examiner* — Brian Whiteman
(74) *Attorney, Agent, or Firm* — MacMillan, Sobanski & Todd, LLC

(57) ABSTRACT

Diabetic wounds have elevated levels of cathepsin K, a protease enzyme, which degrades proteins, such as collagen, causing delayed wound healing. By targeting cathepsin K, diabetic wound healing is ameliorated. Methods and devices for treatment include intradermal injection of odanacatib at or adjacent a wound. Methods and devices for treatment include topical application of pharmacological inhibitors of cathepsin K, for example, in the form of gel, powder, or bandage. Other methods and systems include localized genetic knock out of the cathepsin K gene by topical application of a small interfering RNA (siRNA) or antisense oligonucleotide to aid in wound healing.

34 Claims, 10 Drawing Sheets
(5 of 10 Drawing Sheet(s) Filed in Color)

(56) References Cited

OTHER PUBLICATIONS

Nair, et al., "Targeting Cathepsin K to Facilitate Diabetic Wound Healing", presentation at Wyoming Sensory Biology Symposium, Sep. 2018.

Drake et al., "Cathepsin K Inhibitors for Osteoporosis: Biology, Potential Clinical Utility, and Lessons Learned", Endocrine Reviews, vol. 38, pp. 325-350, 2017.

\* cited by examiner

METHODS OF TREATING WOUNDS USING CATHEPSIN K INHIBITORS

CROSS-REFERENCE TO RELATED APPLICATIONS

This application is a continuation-in-part of U.S. Ser. No. 16/121,443 filed Sep. 4, 2018, now U.S. Pat. No. 10,758,559 issued Sep. 1, 2020, which claims priority to U.S. Application 62/553,702 filed Sep. 1, 2017. This application also claims priority to U.S. Application 62/894,679 filed Aug. 30, 2019, the entire disclosures of which are expressly incorporated herein by reference.

STATEMENT REGARDING FEDERALLY SPONSORED RESEARCH

This invention was made with government support under Grant No. #2P20GM103432, awarded by the National Institutes of Health. The government has certain rights in the invention.

BACKGROUND

Non-healing wounds are a serious complication of diabetes mellitus. Effective treatment of diabetic wounds and related conditions is aided by understanding the pathophysiology and cellular signaling pathways causing the disease and its effects. Research into molecules that can function to inhibit or augment such pathways has shown promise for the treatment of diabetes. However, despite advances in research, there are few options for treating non-healing diabetic wounds. Thus, there is a need for methods and compositions to ameliorate and treat wounds in diabetic subjects.

SUMMARY

Compositions, structures, and methods for use in wound healing, by modulating cathepsin K, are provided herein. The features provided by the embodiments described will be more fully understood in view of the following detailed description, in conjunction with the drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

The embodiments set forth in the drawings are illustrative and exemplary in nature and not intended to limit the subject matter defined by the claims. The following detailed description of the illustrative embodiments can be understood when read in conjunction with the following drawings.

DETAILED DESCRIPTION

General Description

Figure 1A:
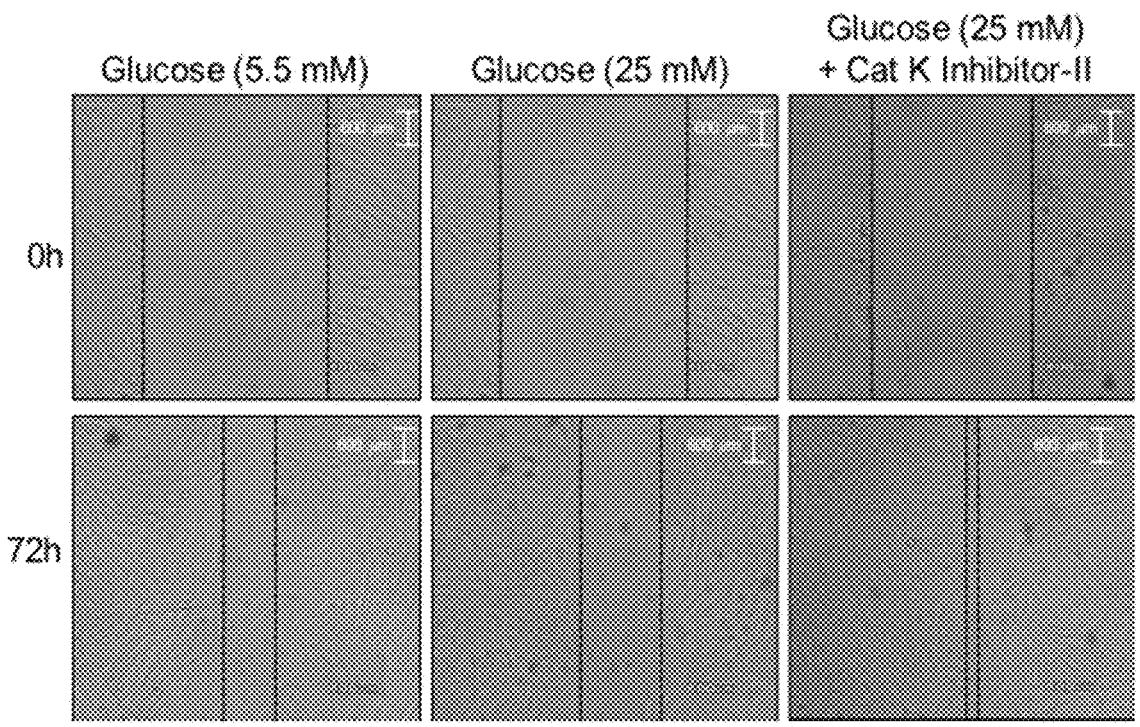
FIG. 1A shows images from a monolayer wound-healing assay comparing treatment groups.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

As used herein, the term "effective amount" means that amount of a drug or pharmaceutical agent that will elicit the biological or medical response of a tissue, system, animal or human that is being sought, for instance, by a researcher or clinician.

Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The term "prophylaxis" includes prevention and refers to a measure or procedure which is to prevent rather than cure or treat a disease. Preventing refers to a reduction in risk of acquiring or developing a disease causing at least one clinical symptom of the disease not to develop in a subject that may be exposed to a disease causing agent or a subject predisposed to the disease in advance of disease outset.

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, "pharmaceutically acceptable excipients" includes all diluents, carriers binders, glidants and other components of pharmaceutical formulations with which the compound of the invention is administered.

Generally, the compound is administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

As used herein, the terms "treating", "treat" or "treatment" include administering a protein described herein to thereby reduce or eliminate at least one symptom of a specified disease or condition or to slow progression of the disease or condition.

As used herein, the term "subject" shall be taken to mean any animal including humans, for example a mammal. Exemplary subjects include but are not limited to humans and non-human primates. For example, the subject is a human.

Detailed Treatment of Wounds

The present disclosure provides methods for accelerating and/or improving and/or enhancing healing of wounds.

Wound healing is a complex process comprising a variety of cells and mediators that progresses through a cascade of events involving inflammation, proliferation, angiogenesis, and remodeling.

Persistently elevated protease activity in chronic wounds impedes wound healing. Chronic wounds fail to proceed through the normal phases of wound healing in an orderly and timely manner. Often, chronic wounds stall in the inflammation phase of healing.

During the normal healing process in acute wounds, proteases are tightly regulated by their inhibitors. The cysteine protease cathepsin K is the most potent collagenolytic and elastolytic enzyme in the mammalian species. Collagen, the primary substrate for cathepsin K, plays a critical role in wound healing by facilitating the migration of dermal fibroblasts and keratinocytes and by stimulating vascularization, and granulation tissue formation.

Cathepsin K (CTSK) Cathepsin K (genbank accession no: NM_000396.3 (polynucleotide) and NP_000387.1 (polypeptide)), abbreviated CTSK, is an enzyme which in humans is encoded by the CTSK gene. [P43235 (CATK_HUMAN) Reviewed, UniProtKB/Swiss-Prot; Last modified Mar. 21, 2012. Version 131 or GENBANK AAH16058.1 GI: 16359188; each of which is hereby incorporated by reference.]

The healing of wounds is a highly orchestrated biological process that involves a complex interplay between extracellular matrix (ECM), skin cells and growth factors. Proteases regulate the balance between ECM degradation and deposition, which creates an equilibrium necessary for the timely and coordinated healing of cutaneous wounds. This balance is disrupted in wounds that poorly heal. ECM provides structure and support to cells and facilitates cell signaling that leads to migration, proliferation and collagen synthesis. The most abundant protein in the ECM is collagen, which forms fibers that provide tensile strength to the wound. Type-1 dermal collagen enhances migration of keratinocytes, fibroblasts and endothelial cells, which play a pivotal role in wound re-epithelization, fibroplasia and neo-angiogenesis.

The development of chronic diabetic wounds is characterized by a highly proteolytic microenvironment or 'catabolic state'. The elevated proteolytic activity leads to a continuous breakdown of the extracellular matrix proteins, sustaining a prolonged destructive state that delays wound healing. Collagen is the major extracellular matrix protein which plays a critical role in wound healing and is a major target for proteolysis.

In chronic wounds, protease levels may exceed levels controlled by their respective inhibitors, leading to destruction of extracellular matrix (ECM) and degradation of growth factors and their receptors. The proteolytic destruction of the ECM, including collagen, delays or prevents the wound from moving into the proliferative phase and also attracts more inflammatory cells, further perpetuating the inflammation cycle.

Collagen is involved in all aspects of wound healing including cell differentiation, migration and granulation tissue formation. Although collagen turnover in normal connective tissue is a very slow and controlled process, in chronic nonhealing wounds, the extent of collagen degradation can be extensive, due to the upregulation of proteolytic enzymes that degrade collagen.

Consequently, increased protease levels and decreased collagen levels lead to impaired wound repair in diabetic subjects and animal models of diabetes.

Delayed or impaired wound healing is a severe complication of diabetes often leading to lower limb amputations and diminished quality of life. Non-healing wounds affect about a quarter of people with diabetes and represents a primary cause of about 85% of lower limb amputations. Wounds with enhanced protease activity have a 90% probability that they will not heal without intervention.

Diabetic wounds do not frequently respond to standard wound care such as debridement, compression, moisture balance, and control of bacterial burden. Therefore, successful treatment can instead be directed to correcting underlying biochemical defects.

Cathepsin K is upregulated in the diabetic skin wounds. Excessive cathepsin activity in humans has been associated with osteoporosis, arthritis, and certain bone cancers. As described herein, inhibition of cathepsin K in diabetic wounds facilitates wound healing.

Methods, systems, and compounds are described for inhibiting cathepsin K, a potent protease, in diabetic wounds to aid healing.

The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXAMPLES

Example 1: Pharmacological Inhibition of Cathepsin K Promotes Fibroblast Migration In Vitro Referring now to FIGS. 1A-1B, the in vitro monolayer wound-healing assay mimics cell migration during wound healing. An in vitro monolayer wound-healing assay in cultured human fibroblasts was used to test whether pharmacological inhibition of cathepsin K affected cell migration under high-glucose (25 mM) conditions. Mannitol was included to control for osmotic pressure and hydroxyurea to eliminate the potential effects of cell proliferation.

Figure 1B:
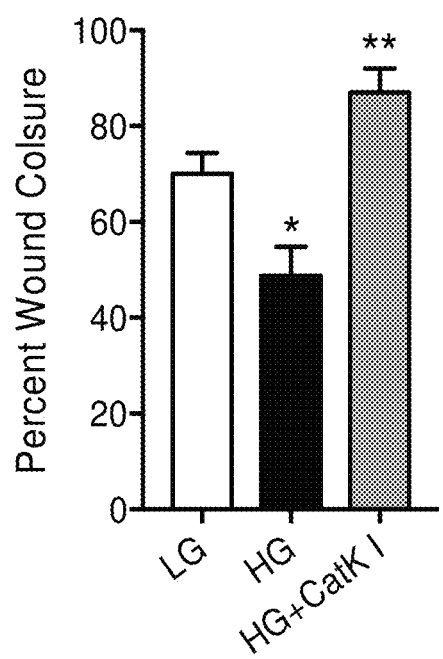
FIG. 1B shows a graph comparing percentage of monolayer wound closure by treatment group.

Cultured fibroblasts, subjected to a high-glucose media, exhibited impaired migration and re-epithelization, as compared to those grown in a normal-glucose (5.5 mM) media. Presence of Boc-I, 1-(N-Benzyloxycarbonyl-leucyl)-5-(N-Boc-phenylalanyl-leucyl) carbohydrazide, Z-L-NHNHCONHNH-LF-Boc), henceforth referred to as cathepsin K inhibitor II), not only reconciled the effects of high glucose, but also increased migration beyond that observed in the cells treated with a low-glucose media, as shown in FIGS. 1A-1B, indicating that inhibition of cathepsin K facilitates epithelization and wound healing under high-glucose conditions.

Referring again to FIGS. 1A-1B, inhibition of cathepsin reverses the inhibitory effect of high glucose (HG) on cell migration in a monolayer wound-healing assay. Confluent human fibroblasts were serum starved and subjected to a media containing low (5 mM, LG) or high (25 mM, HG) glucose. The cell monolayer was wounded with a linear scratch using a sterile pipette tip and treated with 100 ng/ml of cathepsin K inhibitor-II in the presence of 5 μg/ml hydroxyurea. At 0 time (upper left panel) and 72 h (lower left panel) after wounding, the cells were photographed using an inverted microscope equipped with a digital camera. Scale bar=600 μm. FIG. 1A. Representative phase-contrast images for each treatment group. FIG. 1B. Bar graph represents the percentage wound closure 72 h after wounding as measured using the NIH Image J software and represented as mean±SEM, n=6, *p<0.01 compared to LG; **p<0.05 compared to LG.

Figure 2A:
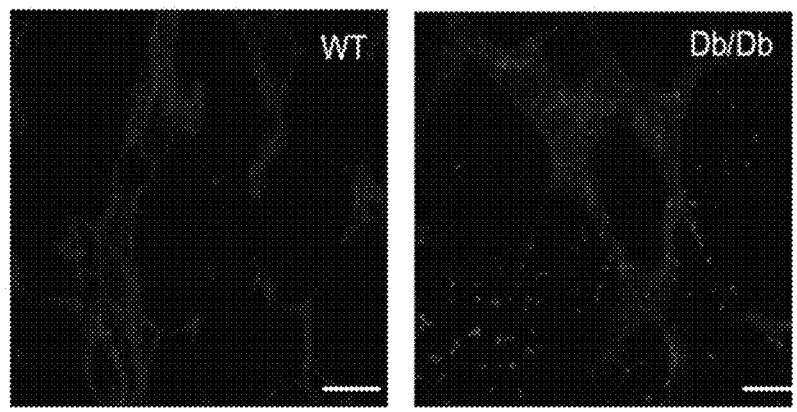
FIG. 2A depicts representative immunostaining of cathepsin K in skin tissues for wild-type (WT) and db/db mice 3 d following wounding.
Figure 2B:
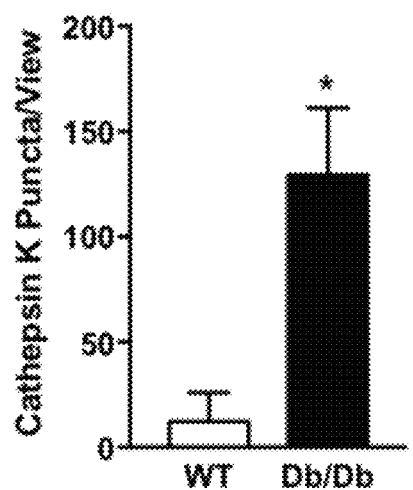
FIG. 2B shows a bar graph comparing protein levels of cathepsin K in wounds in wild-type and diabetic mouse models.
Figure 2C:
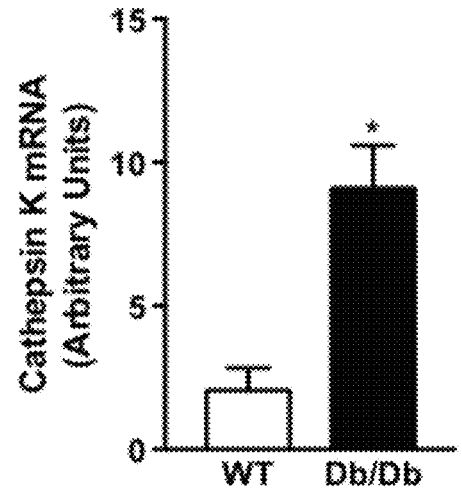
FIG. 2C shows Cathepsin K mRNA levels from WT and db/db mice.

Example 2: Cathepsin K mRNA and Protein Levels are Elevated in the Diabetic Wound Referring to FIGS. 2A-2C the expression levels of cathepsin K were investigated in wounds from wild-type and leptin receptor-deficient diabetic (db/db) mice—an established model of deficient wound-healing associated with diabetes. Consistent with previous studies with scar tissue in the skin, cathepsin K protein and mRNA levels were significantly higher in the wound tissue of db/db mice compared to its wild-type (WT) littermates as evidenced in the immunohistochemical images (FIGS. 2A-C). The results were verified by an independent laboratory.

Constitutive expression of cathepsin K was weak in uninvolved skin from diabetic mice (data not shown). Consistent with the protein levels, a robust elevation in cathepsin K mRNA levels was observed in the wound tissue of db/db mice compared to the wild type. These data indicate a diabetes-associated dysregulation of cathepsin K protein levels in the skin wound and show that cathepsin K is upregulated in the diabetic wound. The data presented in FIGS. 2A-2C is from skin tissues taken on the 5th day following injury. Qualitatively similar data were obtained from tissues obtained 12 days' post injury.

Referring again to FIGS. 2A-2C, Cathepsin K is elevated in wound tissues from diabetic (db/db) mice. FIG. 2A. Representative immunostaining of cathepsin K in skin tissues five days following wounding. Scale bar 2 μm FIG. 2B. Quantification of cathepsin K-positive puncta per high power field, and FIG. 2C. Cathepsin K mRNA levels in 3-day-old wound tissue from wild-type (WT) and db/db mice. Data in the bar graphs are expressed as mean±SEM, n=6, *p<0.001.

Figure 3A:
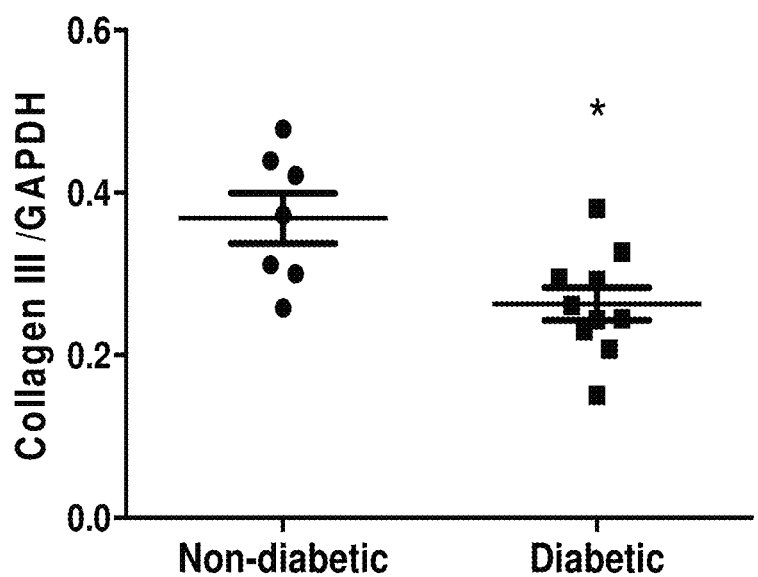
FIG. 3A depicts protein expression levels for collagen in human skin from non-diabetic and diabetic subjects.
Figure 3B:
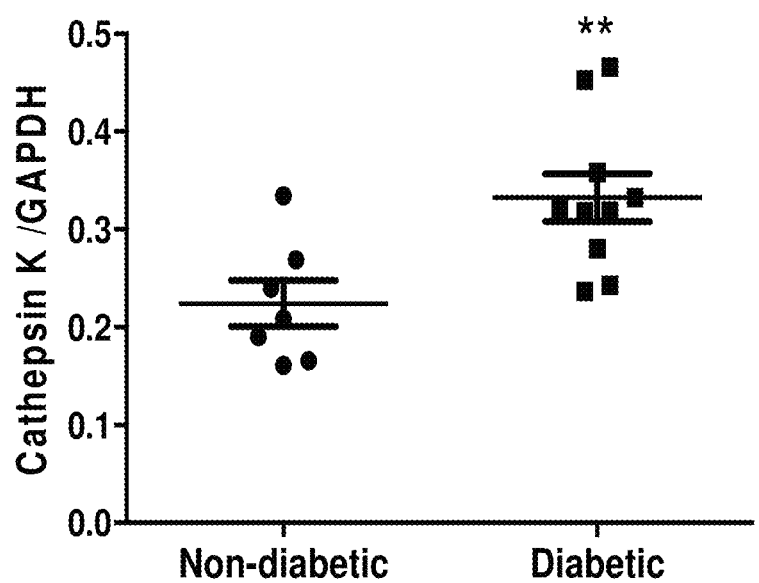
FIG. 3B depicts protein expression levels for Cathepsin K in human skin from non-diabetic and diabetic subjects.

Example 3: Skin Samples from Diabetic Subjects have Lower Levels of Collagen and Elevated Levels of Cathepsin K FIGS. 3A-3B illustrate the expression levels of cathepsin K and collagen proteins in human diabetic and non-diabetic skin samples (courtesy, National Disease Research Interchange). The diabetic skin had significantly decreased collagen levels compared to nondiabetic skin and elevated levels of cathepsin K.

Western blot for collagen (FIG. 3A) and cathepsin K proteins in human skin from non-diabetic and diabetic subjects. FIG. 3A shows mean collagen expression levels were significantly lower in (*p<0.01) in the diabetic skin (n=7) compared to the non-diabetic skin (n=10). FIG. 3B, in contrast, shown cathepsin K levels were significantly elevated in (**p<0.001) in the diabetic skin.

Figure 4:
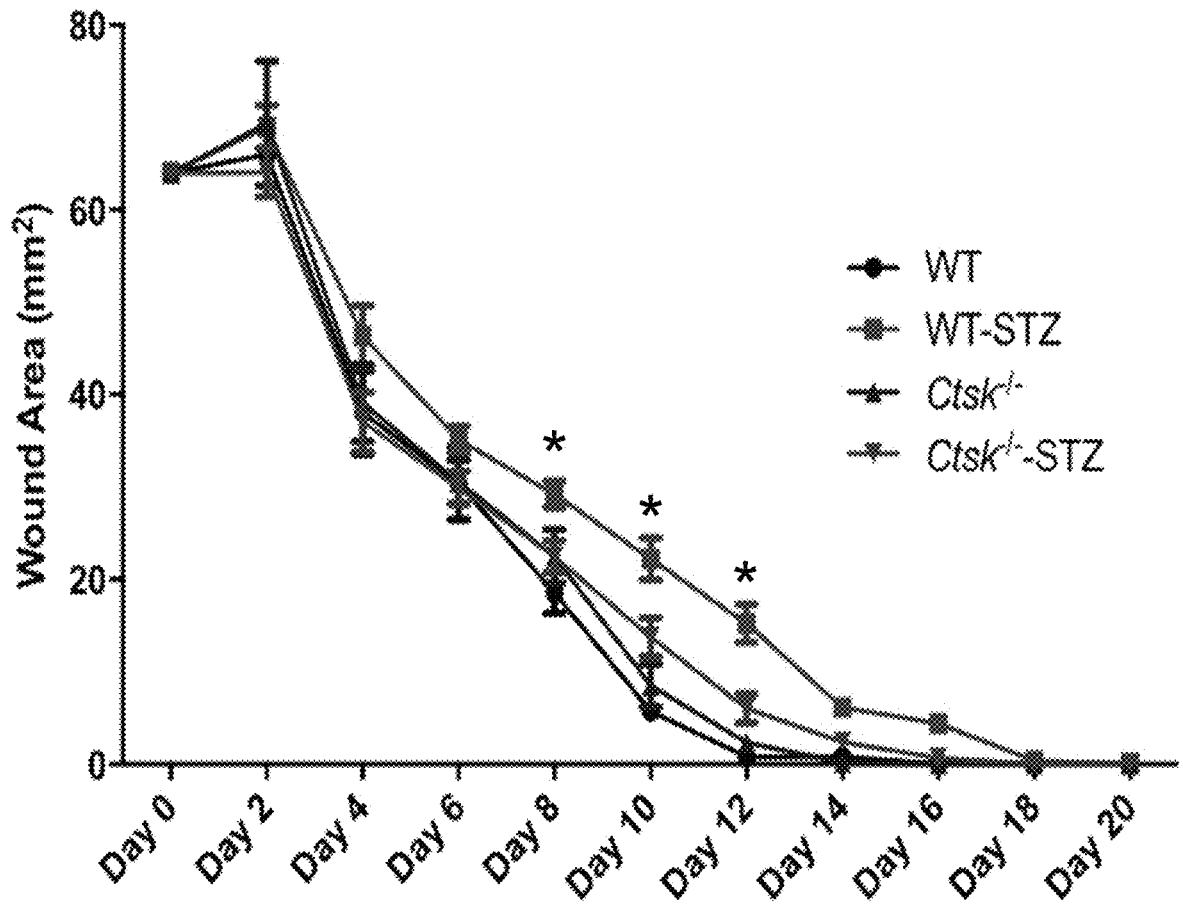
FIG. 4 depicts a graph comparing wound healing over time for WT and cathepsin K knockout mice in a chemically (streptozotocin)-induced diabetic model.

Example 4: Knockdown of Cathepsin K Gene Accelerates Wound Healing in Diabetic Mice FIG. 4 depicts the acceleration of wound healing in streptozotocin-induced diabetes in cathepsin K knockout mice compared to wild-type mice. Mice were rendered diabetic by subjecting them to intraperitoneal injection of streptozotocin (STZ). Four weeks after injection of STZ, a full thickness 8 mm excisional wound was created on the dorsum of the mice. As early as 8-days post wounding, cathepsin K knockout mice exhibited significant reduction in wound surface area as compared to the wildtype mice. Data obtained in this graph is the mean wound area from n=8-10 mice. It is pertinent to note that due to increased mortality of mice treated with STZ, additional mice numbers were included (over those determined by power analysis) in the STZ-treatment group and the experiment was repeated. Also, the mice treated with streptozotocin had severe weight loss and were very lean, which made the accurate assessment of wound dimension a challenge.

Figure 5:
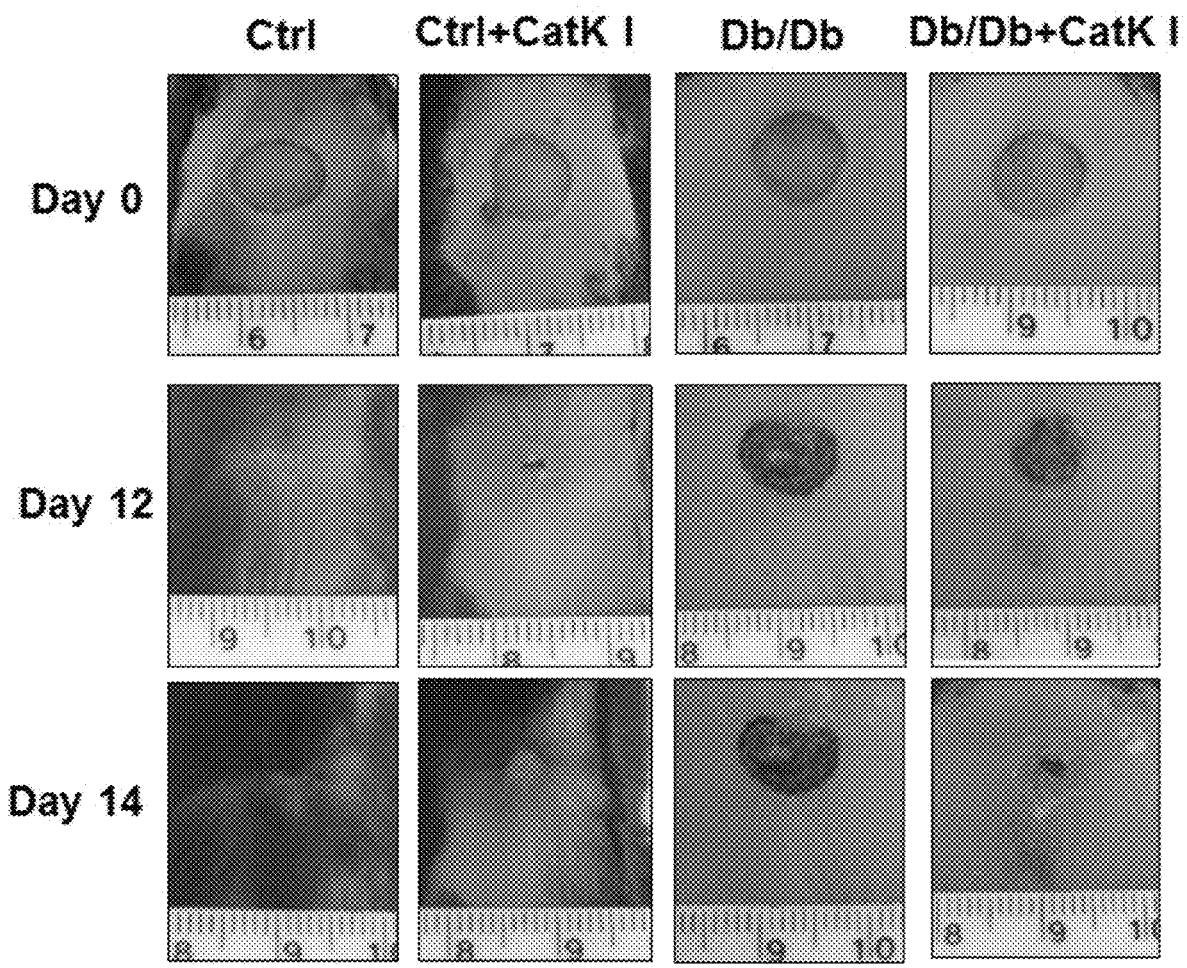
FIG. 5 shows images comparing wound healing in genetically diabetic (db/db) mice over time in response to treatment with vehicle and cathepsin K inhibitor.

Example 5: Pharmacological Inhibition of Cathepsin K Facilitates Wound Healing in Genetically Diabetic (Db/Db+/+) Mice FIG. 5 illustrates the effect of a topically delivered pharmacological inhibitor of cathepsin K on wound healing in genetically diabetic mice. Excisional skin wounds were created in genetically diabetic db/db mice and the wounds were treated along the circumference of the wounds with cathepsin K inhibitor II or vehicle. Wound healing was evaluated by measuring the wound closure rate and histomorphometric analysis. As evidenced by FIG. 5, diabetic mice receiving the inhibitor exhibited significant resolution of wound by day 12 and by day 15 almost complete resolution was observed. In contrast, wounds in the vehicle treated group remain unhealed during this time period. Heterozygous (db/db$^{+/-}$) mice were used as controls in these studies.

Example 6: Evaluation of Cathepsin K in Diabetic Wound Healing in a Porcine Model Dysregulated cathepsin K in diabetic wound healing is modeled using recombinant cathepsin K. Exogenously applied cathepsin K impairment in diabetic wound healing is evaluated.

Using a clinically-relevant porcine model, the role of cathepsin K in diabetic wound healing is evaluated. Specifically, assessment is made of the causal relationship between increased cathepsin K and impairment in diabetic wound healing by attenuating collagen deposition, vascularization and granulation tissue formation.

The relationship between of cathepsin K levels and diabetic wound healing in a clinically relevant porcine model of diabetic wound healing is evaluated.

Anatomical and physiological similarities between pig and human skin make pigs an appropriate model for wound healing studies and have been extensively used in the literature. Like humans, pigs have a relatively thick epidermis with sparse hair growth and the skin is adherent to underlying structures (does not slides over the subcutaneous fascia). Additionally, the collagen type and the turnover time of the pig epidermis (30 d) is approximately similar to that of the human skin. Furthermore, the immune cells in skin of the pigs are similar to those in human skin. These characteristics make the pig model of wound healing and appropriate and relevant model to mimic human wound healing.

Using female domestic pigs, a diabetic phenotype is induced with Streptozotocin (STZ) injections. The animals are anesthetized with intramuscular injections of ketamine 10 mg/kg, xylazine 5 mg/Kg and acepromazine 0.2 mg/kg, followed by a complete general anesthesia induced by mask inhalation of 1-2% isoflurane. A central venous catheter is placed and streptozotocin is administered intravenously (150 mg/kg, 1 g STZ in 10 mL sodium citrate buffer freshly prepared, given over 10 min). To avoid hypoglycemia due to insulin released by the destroyed beta-cells, 200 mL of a 5% glucose solution is given over 1 h period after STZ injection. The diabetic phenotype develops within 4 weeks.

Following induction of anesthesia, the dorsal skin of the pig is shaved, and each animal is reproducibly subjected to ten-full-thickness one-inch square excisional skin wounds (~300 m thickness) using a scalpel. The wounds are spaced a minimum of 2-cm apart and in two columns on each side of the dorsal thoracolumbar midline. All wounds are dressed with an occlusive dressing. Wound photographs are taken immediately after wounding and on day 0, 7, and 14 with a camera mounted on a tripod at a fixed distance. Time to wound closure (# of days for complete reepithelialization) and % wound closure (1−[wound area/original wound area]) is determined. Imaging software calculates the wound area for each pig and measurements of changes over time.

Fifteen days after wounding the animals are euthanized with an overdose of sodium pentobarbital (100 mg/kg, intravenous). Wounds are harvested with at least 1-cm of surrounding healthy tissue at the depth of the muscle fascia and subject to analysis.

Epithelial gap, granulation tissue, vascularization, and collagen content is assessed. Deparaffinized skin-tissue sections are stained with H&E and are analyzed for the epithelial gap (distance between the advancing edges of keratinocyte migration and granulation tissue). Vascularization is detected by staining with CD31 antibody. Collagen content is determined by staining the section with Picro-Sirius and total ECM content is analyzed by Mason-Goldner trichome staining.

Tissue analysis is performed and mRNA and protein levels of cathepsin K is determined by quantitative RT-PCR and Western analysis respectively. Cathepsin K activity is determined using a fluorescence-based assay (Abcam). For immunohistochemical detection of cathepsin K, tissue sections are probed with anti-cathepsin K antibody followed by Alexa-Fluor-594 AffiniPure donkey anti-rabbit IgG.

Wound inflammation, proinflammatory cytokine and oxidative stress is assessed. Wound tissues are homogenized, sonicated, centrifuged and supernatants subjected to multiplex ELISA for different cytokines (BioRad, Bioplex-Pro). Specifically, the levels of IL-6, TBFβ1, and VEGF are determined. The levels of malondialdehyde and the activities of GSH-Px and catalase in the wounds are determined.

Example 7: Dysregulated Cathepsin K in Diabetic Wound Healing May be Ameliorated Using Cathepsin K siRNA Knockdown of cathepsin K using siRNA may be used to facilitate wound closure and promote healing of diabetic wounds.

Previous studies have shown that an n=8-10 wounds are sufficient to declinate statistically significant differences in wound healing (Singer and McClain, S. A. *Acad Emerg Med.* 10: 1029-33, 2003; Long, et. al, *J Control Release* 253: 73-81, 2017; Hamed et. al. *Diabetes.* 66: 2254-65, 2018). We have six groups collectively for Example 6 & 7: 1) Vehicle for streptozotocin (STZ) 2) STZ-treated 3) STZ+ vehicle for recombinant cathepsin K 4) STZ+ recombinant cathepsin K 5) STZ+ scrambled siRNA and 6) STZ+ cathepsin K siRNA. Previous studies have shown that an n=8-10 wounds are sufficient to declinate statistically significant differences in healing. Consequently, 6 pigs (a sample size of 60 wounds) are assessed in the study.

This study involves three experimental groups—five STZ-treated pigs each of the following groups: cathepsin K inhibitor, cathepsin K siRNA, and miR-146a. Anesthesia is induced as described using ketamine, xylazine, and acepromazine injection. Following induction of anesthesia, the dorsal skin of the pig is shaved, depilated and prepped with chlorhexidine or betadine. Each animal is reproducibly subjected to ten full-thickness skin wounds one-inch square wounds (~300-micrometer thickness) using a scalpel. The wounds are spaced a minimum of two centimeters apart and created in two columns on each side of the dorsal thoracolumbar midline. Wounds are treated with intradermal injections (using a Hamilton Syringe) of either 50 µl vehicle (phosphate buffered saline) or 10 µM solution of cathepsin K inhibitor II in DMSO+PEG (20:80) or scrambled or cathepsin K siRNA (200 pico g) liposomes. All wounds are dressed with an occlusive dressing (Tegaderm; 3M, St. Paul, Minn.). Wound photographs are taken immediately after wounding and on day 0, 7, and 14, with a camera mounted on a tripod at a fixed distance. Animals also receive additional doses of the treatment at the same time. Animals are anesthetized prior to taking pictures. On day 15 following wounding, animals are euthanized with an overdose of sodium pentobarbital (100 mg/kg) administered intravenously. The wounds are harvested with at least 1 cm of surrounding healthy tissue at the depth of the muscle fascia and are used for analysis.

Agarose siRNA liposomes are formulated. A 1% sterilized stock solution of low-melting-point agarose VII is diluted to 0.4% (w/v) using prepared siRNA-liposomes complexed with Lipofectamine-2000 (ratio of 600 pmol siRNA to 0.5 mL lipofectamine). As a marker for skin penetration, a fluorophore-tagged siRNA, siGLO Red is included in the siRNA-liposomal complex.

One pig is used for each vehicle, recombinant cathepsin K, scrambled siRNA, and cathepsin K siRNA treatments (total of four pigs). Wounding is done as described in Example 6. Recombinant cathepsin K (50 µL of 20 µg/mL) is applied topically to the wounds in a radial pattern using a Hamilton syringe on a daily basis. For siRNA studies, 200 pmol cathepsin K siRNA or 200 pmol scramble siRNA in the liposomal formulation is applied to the wounds (in a total volume of 10 µL) immediately after wounding and once every 3 days. Pigs are anesthetized with isoflurane on days 3, 9, and 12 and wounds are photographed. Time to wound closure epithelial gap, granulation tissue, vascularization, collagen content and cathepsin K levels are analyzed as described above.

In non-diabetic pigs the time to wound closure, a definitive measure of complete re-epithelialization is ~12-14 days whereas diabetic pigs generally take a longer (~21 days). Evaluation of a reciprocal relationship between wound cathepsin K levels and collagen is assessed. The comparative healing time for wounds treated the pharmacological inhibitor or cathepsin K siRNA to exhibit complete re-epithelization is assessed. Additionally, increases in neovascularization and increases in granulation tissue in the animals receiving cathepsin K inhibitor and siRNA is compared.

An important role of cathepsin K diabetic wound healing is assessed and siRNA mediated knockdown of cathepsin K to accelerate diabetic wound healing by increasing wound collagen content, reducing inflammation, enhancing wound angiogenesis and re-epithelization of the wound. Diminished cathepsin K levels in the wound may facilitate wound healing.

Further assessment of cathepsin K and/or compensatory upregulation of other cathepsins or proteases including MMPs (MMPs are known to be cleaved and regulated by cathepsin K) are assessed by measuring levels of other key cathepsins and MMPs in the diabetic wound. Also, cystatin C, the endogenous inhibitor of cathepsin K may be upregulated in response to exogenous cathepsin K, and measures for cystatin C are included.

The efficacy of the siRNA and recombinant cathepsin K may be measured or modulated. Previous studies have shown that a 50% reduction in reporter gene may be required to produce therapeutic effects for other skin disorders. The addition of a chemical penetration enhancer, such as propylene glycol or commercially available Accell™-siRNA may be used to enhance cellular uptake and improve the efficacy of gene silencing.

Example 8: Evaluation of Mechanisms of Action

Without wishing to be bound by theory, the mechanisms of action of targeting cathepsin K in wound healing are discussed. Mechanisms by which targeting cathepsin K facilitates wound healing involve cell types in the diabetic wound that express cathepsin K.

The inventor's research has produced a cardiomyocyte-specific cathepsin K knockout mice knockout using the Cre-Lox system and found that this conditional knockout protects against doxorubicin-induced cardiotoxicity. Using the whole-body knockout of cathepsin K and conditional knockouts of cathepsin K. A conditional knockout of cathepsin K using the Cre-Lox system can be used to knockout cathepsin K in selective cell types.

Additionally, upstream signals (proinflammatory cytokines, oxidative stress) and downstream effectors of cathepsin K are relevant. Oxidative stress causes the release of cathepsin K from the lysosomes of cardiomyocytes which subsequently cleaves and activates caspases, causing apoptosis. Similar pathways in wound tissue may be relevant. The stromal-derived factor (SDF-1α) is an important regulator of epidermal cell migration and angiogenesis associated with wound repair. In neuroblastoma cells, SDF-1α serves as a substrate for cathepsin K. Lower levels of SDF-1α may be associated with a reciprocal increase in cathepsin K in wound samples from diabetic mice (data not shown). Primary neonatal human epithelial keratinocytes and diabetic human adult epithelial keratinocytes may be used to further explore the mechanisms by which cathepsin K regulates wound healing.

Example 9: Approaches to Targeting Endogenous Cathepsin K

Cathepsin K is a cysteine protease with potent collagenolytic and elastolytic activity. It is unique among collagenases in its ability to cleave type I collagen. Cathepsin K is highly expressed in dermal fibroblasts of surgical scars, while its levels are quite low in the normal skin. Although cathepsin K is localized in the lysosomes, the inventor's research has shown that cathepsin K translocates to the cytoplasm under conditions of cellular stress. Recent studies have attempted the modulation of matrix metalloproteases and neutrophil elastases to aid in wound healing. However, unlike matrix metalloproteases and neutrophil elastases, cathepsin K can function both as an extracellular collagenase that can break down ECM, and an intracellular collagenase that can degrade endocytize collagen, which renders it a more attractive target. Methods are provided for inhibition of cathepsin K to prevent the degradation of collagen in the wounds and thereby facilitate wound healing.

Microinjection of a pharmacological inhibitor of cathepsin K is a method to facilitate wound healing.

Inhibition of gene expression via topical administration of cathepsin K siRNA is a method to facilitate wound healing. Once inside the cell, the topically administered siRNA degrades its endogenous mRNA, thereby knocking down the target gene for post-transcriptional gene silencing and treating diabetic wounds. The siRNA molecules can achieve >80% target protein inhibition at nanomolar concentrations, and their enhanced intracellular stability enables knockdown that can last for weeks in nondividing cells. Moreover, the silencing is transient and local, alleviating concerns of prolonged action and off-target effects.

Delivery methods to enhance penetration of the skin, provide effective mechanisms for sustained delivery, and overcome negative charge of the wound, increase efficacy for topical siRNA. To overcome these issues, methods are provided using a topical agarose matrix-based siRNA delivery system that reproducibly delivers siRNA into the skin tissue. This technique has been successfully used to silence several proinflammatory genes (e.g. p53, Smad3, Keap1, nrf2) and to promote remodeling and wound closure. Cathepsin K is overexpressed in the inflamed skin, particularly in skin fibroblasts and keratinocytes. Methods of treatment are provided for inhibiting this potent, proinflammatory protease to facilitate diabetic wound healing. Wounds are a type of condition characterized by cell or tissue damage. Wound healing is a dynamic pathway that optimally leads to restoration of tissue integrity and function. The wound healing process consists of three overlapping phases. The first phase is an inflammatory phase, which is characterized by homeostasis, platelet aggregation and degranulation. Platelets as the first response, release multiple growth factors to recruit immune cells, epithelial cells, and endothelial cells. The inflammatory phase typically occurs over days 0-5. The second stage of wound healing is the proliferative phase during which macrophages and granulocytes invade the wound. Infiltrating fibroblasts begin to produce collagen. The principle characteristics of this phase are epithelialization, angiogenesis, granulation tissue formation and collagen production. The proliferative phase typically occurs over days 3-14. The third phase is the remodeling phase where matrix formation occurs. The fibroblasts, epithelial cells, and endothelial cells continue to produce collagen and collagenase as well as matrix metalloproteases (MMPs) for remodeling. Collagen crosslinking takes place and the wound undergoes contraction. The remodeling phase typically occurs from day 7 to one year.

Compounds and compositions described herein can be used for promoting wound healing (e.g., promoting or accelerating wound closure and/or wound healing, mitigating scar fibrosis of the tissue of and/or around the wound, inhibiting apoptosis of cells surrounding or proximate to the wound). Thus, in certain embodiments, the present invention provides a method for promoting wound healing in a subject, comprising administering to the subject a compound, or pharmaceutically acceptable salt or composition thereof. The method need not achieve complete healing or closure of the wound; it is sufficient for the method to promote any degree of wound closure. In this respect, the method can be employed alone or as an adjunct to other methods for healing wounded tissue.

The compounds and compositions described herein can be used to treat wound during the inflammatory (or early) phase, during the proliferative (or middle) wound healing phase, and/or during the remodeling (or late) wound healing phase.

Example 10: Inhibition of Cathepsin K in Diabetic Wound Healing

As discussed previously in Examples 6 and 7, a porcine model is useful for evaluating skin healing and wound closure. Using a porcine diabetic wound healing model, treatment with either CatKI-II or odanacatib were shown to facilitate wound closure, as shown in FIGS. 6-9.

Odanacatib is a potent and selective inhibitor of cathepsin K and can be administered to promote wound healing in diabetic pigs. Pigs (3-4 months old) were rendered diabetic with intravenous injection of streptozotocin (75 mg/Kg). Four weeks following streptozotocin injections 6-10 full-thickness (one-inch square, ~300 meter thickness) wounds were created in two columns on each side of the dorsal thoracolumbar midline. Wounds were topically treated with vehicle or odanacatib (30 ng/mm$^2$ or 300 ng/mm$^2$ of wound) by intradermal injections along the circumference of the wounds, once on day 0 and on days 3, 7, 14 and 21 post-wounding. Wounds were photographed prior to treatment and analyzed for wound closure rates.

TABLE 1

| Tukey's multiple comparisons test | Summary | P value |
|---|---|---|
| D 3 | | |
| Vehicle vs. CatKI-II (30 µg/mm$^2$) | * | 0.0178 |
| Vehicle vs. CatKI-II (300 µg/mm$^2$) | ns | 0.9641 |
| CatKI-II (30 vs. 300 µg/mm$^2$) | ns | 0.1386 |
| D 7 | | |
| Vehicle vs. CatKI-II (30 µg/mm$^2$) | ns | 0.1185 |
| Vehicle vs. CatKI-II (300 µg/mm$^2$) | ns | 0.6292 |
| CatKI-II (30 vs. 300 µg/mm$^2$) | ns | 0.6182 |
| D 14 | | |
| Vehicle vs. CatKI-II (30 µg/mm$^2$) | * | 0.0124 |
| Vehicle vs. CatKI-II (300 µg/mm$^2$) | ns | 0.6457 |
| CatKI-II (30 vs. 300 µg/mm$^2$) | * | 0.0142 |
| D 21 | | |
| Vehicle vs. CatKI-II (30 µg/mm$^2$) | ** | 0.0051 |
| Vehicle vs. CatKI-II (300 µg/mm$^2$) | ns | 0.8511 |
| CatKI-II (30 vs. 300 µg/mm$^2$) | * | 0.0103 |

Figure 6:
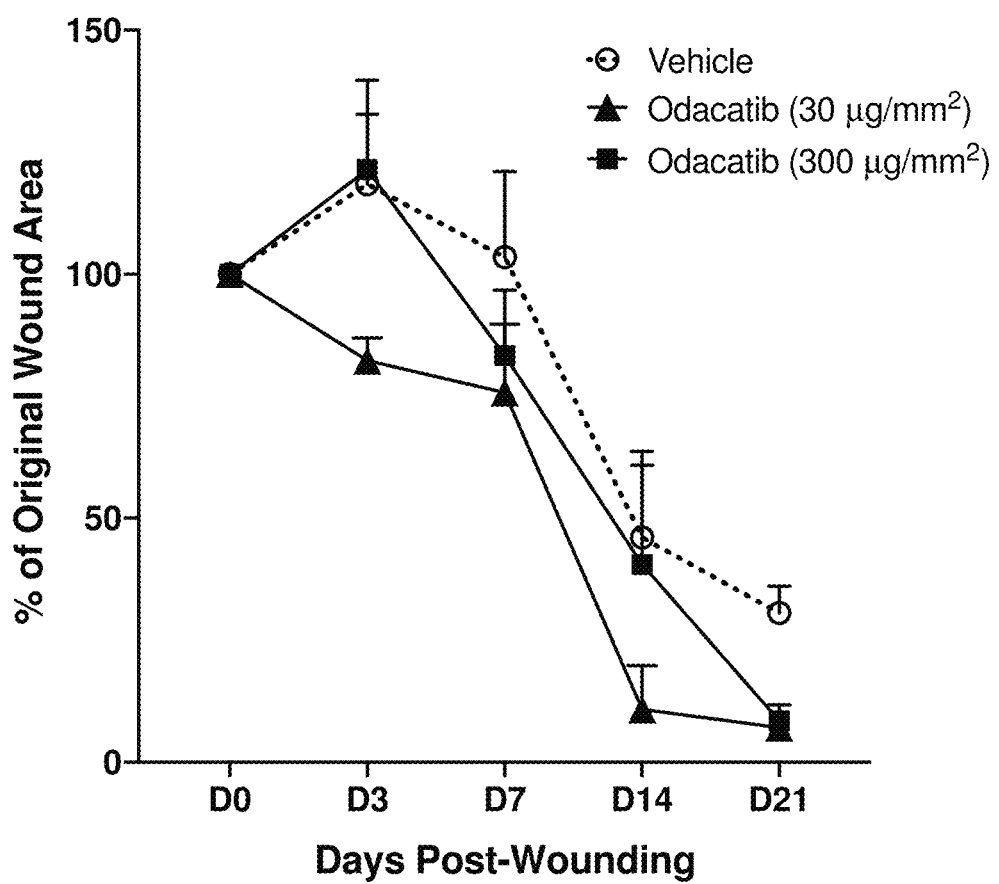
FIG. 6 shows wound area plotted as a function of time for wounds treated with odanacatib.

FIG. 6 shows wound area by time for the odanacatib treatment group. Data are expressed as mean±SEM (n=8 for vehicle and 6 each for odanacatib treatment). Table 1 shows ANOVA followed by post-hoc analysis. Because some values are missing as we had euthanized one pig from each group on day 14 for molecular analysis, the data were analyzed by fitting a mixed model, rather than by repeated measures ANOVA. Wound area analysis revealed that the lower dose (30 ng/mm$^2$/wound) of odanacatib showed statistically significant improvement in wound healing compared to both vehicle and the higher dose (300 ng/mm$^2$/wound) of odanacatib on day 14 post-wounding. On day 21 post-wounding both the higher and lower doses of odanacatib showed significant improvement (~93% wound closure) over vehicle-treated wounds (~70% wound closure).

Figure 7:
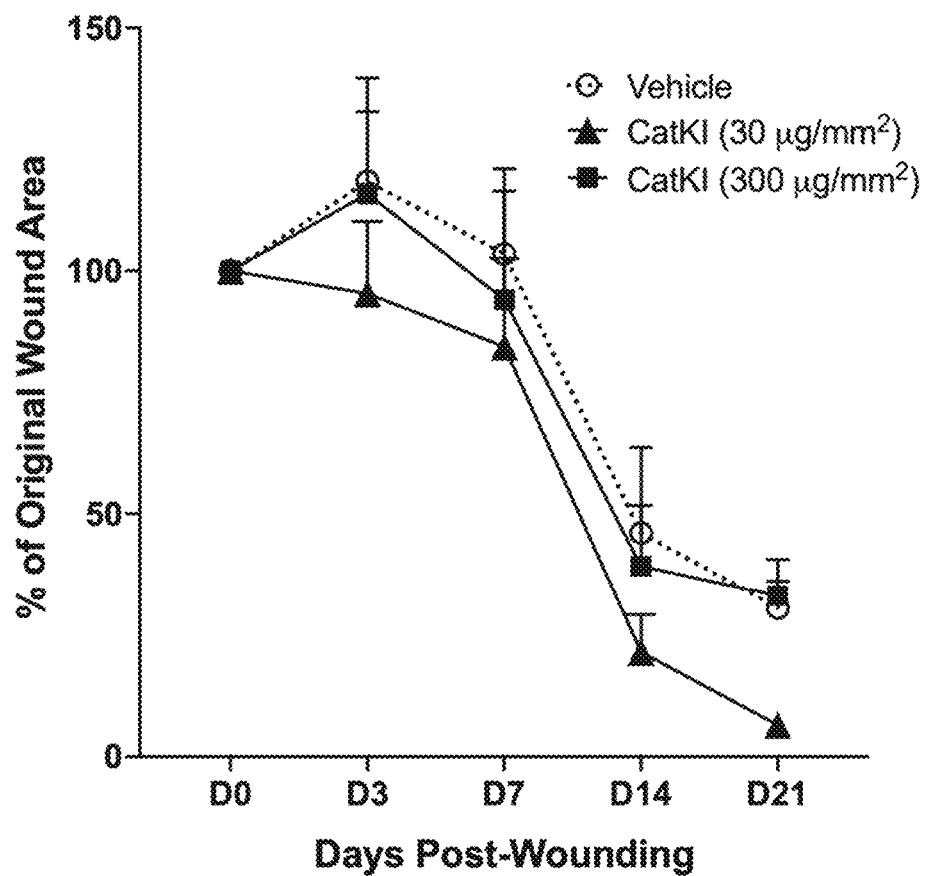
FIG. 7 shows wound area plotted as a function of time for wounds treated with cathepsin K Inhibitor-II.

As shown in FIG. 7, Cathepsin K inhibitor II promotes wound healing in diabetic pigs. Pigs (3-4 months old) were rendered diabetic with intravenous injection of streptozotocin (75 mg/Kg). Four weeks following streptozotocin injections 6-10 full-thickness (one-inch square, ~300 meter thickness) wounds were created in two columns on each side of the dorsal thoracolumbar midline. Wounds were topically treated with vehicle or cathepsin K Inhibitor-II (30 ng/mm$^2$ or 300 ng/mm$^2$ of wound) by intradermal injections along the circumference of the wounds, once on day 0 and on days 3, 7, 14 and 21 post-wounding. For this study, the cathepsin K inhibitor was a cell-permeable peptide-based Cathepsin K Inhibitor II (Boc-I, 1-(N-Benzyloxycarbonyl-leucyl)-5-(N-Boc-phenylalanyl-leucyl) carbohydrazide, Z-L-NHNHCONHNH-LF-Boc) which is a cell permeable cathepsin K inhibitor from Calbiochem (Millipore Sigma). Wounds were photographed prior to treatment and analyzed for wound closure rates.

Data are expressed as mean±SEM (n=8 for vehicle and 6 each for treatment). Table 2 shows ANOVA followed by post-hoc analysis. Because some values are missing as we had euthanized one pig from each group on day 14 for molecular analysis, the data were analyzed by fitting a mixed model, rather than by repeated measures ANOVA.

TABLE 2

| Tukey's multiple comparisons test | Summary | P value |
|---|---|---|
| D 3 | | |
| Vehicle vs. CatKI-II (30 μg/mm$^2$) | * | 0.0178 |
| Vehicle vs. CatKI-II (300 μg/mm$^2$) | ns | 0.9641 |
| CatKI-II (30 vs. 300 μg/mm$^2$) | ns | 0.1386 |
| D 7 | | |
| Vehicle vs. CatKI-II (30 μg/mm$^2$) | ns | 0.1185 |
| Vehicle vs. CatKI-II (300 μg/mm$^2$) | ns | 0.6292 |
| CatK I-II (30 vs. 300 μg/mm$^2$) | ns | 0.6182 |
| D 14 | | |
| Vehicle vs. CatKI-II (30 μg/mm$^2$) | * | 0.0124 |
| Vehicle vs. CatKI-II (300 μg/mm$^2$) | ns | 0.6457 |
| CatKI-II (30 vs. 300 μg/mm$^2$) | * | 0.0142 |
| D 21 | | |
| Vehicle vs. CatKI-II (30 μg/mm$^2$) | ** | 0.0051 |
| Vehicle vs. CatKI-II (300 μg/mm$^2$) | ns | 0.8511 |
| CatKI-II (30 vs. 300 μg/mm$^2$) | * | 0.0103 |

FIG. 7 shows wound area by time for the Cathepsin K inhibitor II treatment group. Wound area analysis revealed that the lower dose (30 ng/mm$^2$/wound) of cathepsin K inhibitor II showed statistically significant improvement in wound healing compared to both vehicle and the higher dose (300 ng/mm$^2$/wound) of cathepsin K inhibitor II on day 21 post-wounding. On day 21 post-wounding both the higher and lower doses showed significant improvement (~93% wound closure) over vehicle-treated wounds (~67% wound closure).

Figure 8:
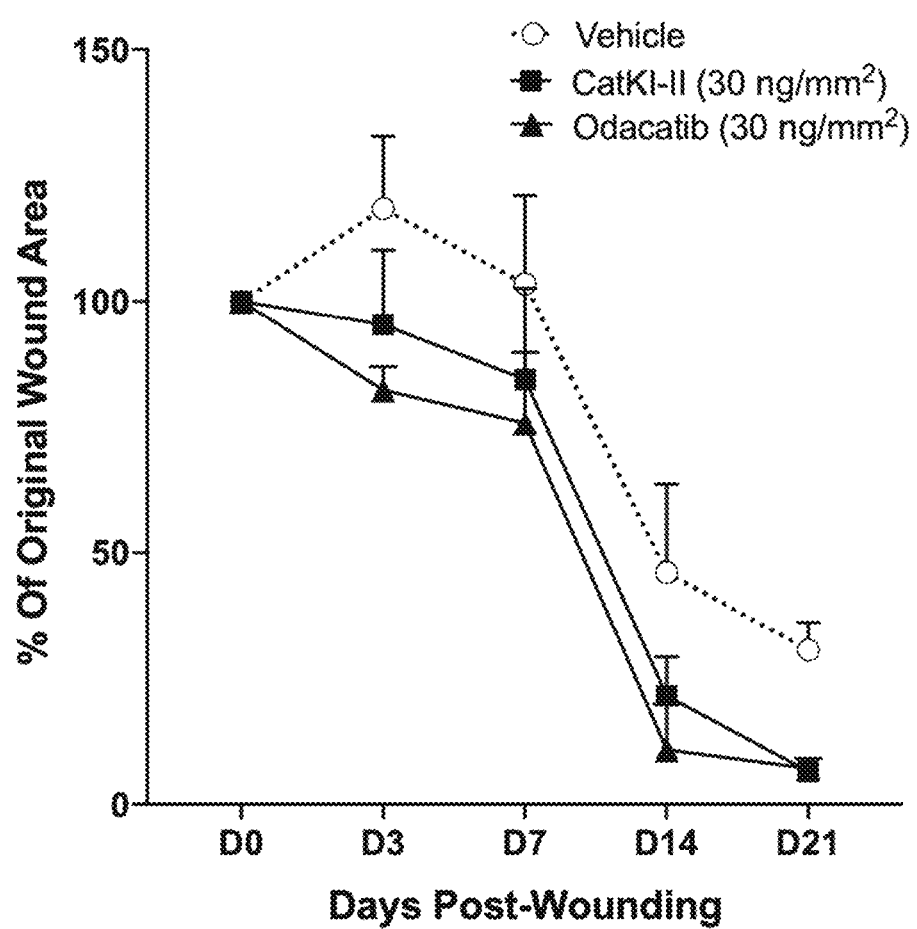
FIG. 8 shows wound area plotted as a function of time comparing wounds treated with Cathepsin K Inhibitor-II or odanacatib.

FIG. 8 compares odanacatib and cathepsin K inhibitor II for promoting wound healing in diabetic pigs. Pigs (3-4 months old) were rendered diabetic with intravenous injection of streptozotocin (75 mg/Kg). Four weeks following streptozotocin injections, 6-10 full thickness (one-inch square, ~300 meter thickness) wounds were created in two columns on each side of the dorsal thoracolumbar midline. Wounds were topically treated with vehicle, cathepsin K inhibitor II or odanacatib (30 ng/mm$^2$) and wound area was determined on days 0, 3, 7, 14 and 21 post-wounding. Data are represented as mean±SEM (n=6-8 wounds per treatment group).

Figure 9:
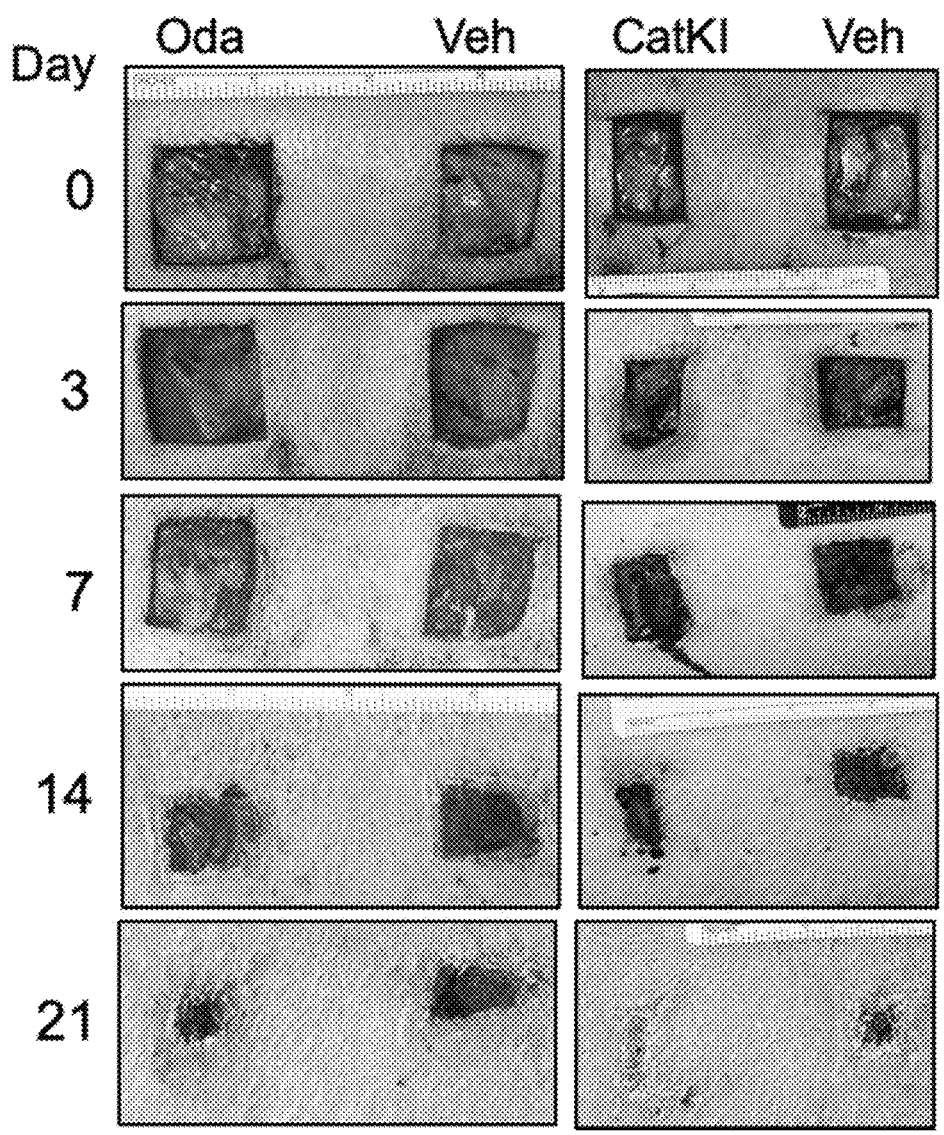
FIG. 9 shows representative images of wounds during treatment with Cathepsin K Inhibitor-II or odanacatib.

FIG. 9 shows representative photographs from one pig each (pig #8367 and 8368 respectively) with odanacatib and cathepsin K inhibitor II (30 ng/mm$^2$) treatment and vehicle control.

Example 11: Dosage Assessment in Accelerating Diabetic Wound Treatment

Dosage comparisons using a porcine model can provide indications of efficacy and minimum effective dose of odanacatib or Cathepsin K inhibitor II for healing diabetic wounds which are relevant and indicative of efficacy and dosage in treatment of human patients.

Previous studies have shown that 6 wounds per dose are sufficient to declinate a 40% difference between the different depths of injury as indicated in previous studies. A detectable difference is based on 90% power, an overall ANOVA significance level of 0.05, and a 0.5 standardized effect. Therefore, a minimum of four pigs (5 concentrations and vehicle=total 6 treatment×6 wounds/treatment=36 wounds) can suffice to assess a dose-response curve for diabetic wound healing by odanacatib and establish the minimum dose of odanacatib that results in complete resolution of diabetic wounds in ≤15 days.

Following induction of anesthesia, the dorsal skin of the pig is shaved, and each animal is reproducibly subjected to ten-full-thickness one-inch square excisional skin wounds (~300 μm thickness) using a scalpel. The wounds are spaced a minimum of 2-cm apart and are created in two columns on each side of the dorsal thoracolumbar midline. The wounds are treated with 0.3 ng/mm$^2$ wound area, 3 ng/mm$^2$ wound area, 30 ng/mm$^2$ wound area, 300 ng/mm$^2$ wound area, and 3000 ng/mm$^2$ wound area by intradermal injections along the circumference of the wound. All wounds are dressed with an occlusive dressing. Wound photographs are taken immediately after wounding and on day 0, 3, 7, 14 and day at which complete wound closure occurs; a ruler is included in the digital photo. Time to wound closure (# of days for complete reepithelialization) and % wound closure (1−[wound area/original wound area]) is determined. Imaging software is used to calculate the wound area for each pig and is plotted as a function of time. Upon wound closure, the animals are euthanized. Wounds are photographed and harvested with at least 1-cm of surrounding healthy tissue at the depth of the muscle fascia and are used for analysis.

Because low levels of proteases and inflammatory responses are beneficial during the early stages of wound healing to facilitate cell migration and proliferation, better outcomes may be achieved when odanacatib is administered after day 3, rather than immediately after wounding. Dosing may be administered in a time-dependent regime, with an initial small dose, a subsequent large dose, and one or more following small doses. In such a dosing regime, non-limiting examples of the large dose may provide odanacatib or cathepsin K inhibitor II in a range of 1.5 to 100 times greater than provided in the one or more small dose. Other non-limiting examples of time-dependent dosing can be 2, 3, 4, 5, 6, 7, 8, 9, 10 etc. to 99 times greater.

Example 12: Wound Treatment

The term "wound" refers to an injury to a body tissue. Non-limiting examples of wounds which can be treated in accordance with the present invention are: abrasions, aseptic wounds, burns, contused wounds, incised wounds (incisions), excised wounds (excisions), lacerated wounds, non-penetrating wounds (i.e., wounds in which there is no disruption of the skin but there is injury to underlying structures), open wounds, penetrating wounds, perforating wounds, puncture wounds, septic wounds, sores, subcutaneous wounds and skin/external/dermal/epidermal ulcers.

Non-limiting examples of sores are bed sores, cancer sores, chrome sores, cold sores, pressure sores etc. Therefore as mentioned above, in the present context the term "wound" encompasses the term "ulcer", "lesion", "sore" and "infarction".

The wound may also be due to a disorder (such as diabetes), an infectious lesion, surgery, a puncture, a chronic wound, or a scar. The wound may be a chronic skin ulceration, a sore, a dermal wound, or an epidermal wound. The wound may be due to destructive wound inflammation, delayed or impaired healing, or disturbed tissue regeneration. The wound may be located internally or externally of a subject.

The term "wound" will be taken to mean any injury in which a tissue of a subject is compromised (e.g., torn, pierced, cut, or otherwise broken).

As used herein, the term "dermal wound" shall be taken to mean a lesion to one or more layers of skin of a subject, e.g., wherein the lesion comprises one or more apoptotic dermal cells and/or one or more necrotic dermal cells. The term "dermal wound" shall be taken to include a wound that affects an epidermal layer of a subject and/or a dermal layer of a subject and/or a hypodermal layer of a subject.

The term "chronic wound" refers to a wound that does not heal in an orderly set of stages and in a predictable amount of time. Generally, wounds that do not heal within three months are considered chronic. Chronic wounds include, but are not limited to, e.g., diabetic ulcers, pressure ulcers, etc. An acute wound can develop into a chronic wound.

The term "acute wound" or "normal wound" refers a wound that undergoes normal wound healing repair.

The term "progression of a wound" will be understood to mean a worsening of a wound, e.g., increasing in size and/or depth and/or progression to a more advanced stage and/or development of an infection.

The term "healing" in the context of the present disclosure is a promotion or acceleration of the time from when the compound is administered until significant or complete wound closure (full wound contraction).

While elevated and prolonged expression of protease can delay wound healing, during the early phase of wound healing, the degradation and remodeling of the ECM by proteases, plays a critical role in the process of tissue repair by promoting the influx of leukocytes, angiogenesis and re-epithelialization. Therefore, the time of administration of odanacatib or other cathepsin K inhibitors is relevant to its beneficial effects on the healing of diabetic wounds. Thus, the kinetics of wound healing in response to dose timing of odanacatib post-wounding with various times of administration are assessed. The first dose may be delayed until 2-7 days after the initial wounding.

Understanding the molecular changes in the wound in response to odanacatib administration provides an objective understanding of the healing time. Additionally, it elucidates the molecular mechanisms by which inhibition of cathepsin K improves wound healing. For this assessment, epithelial gap, cathepsin K activity, pro-inflammatory cytokines, collagen content and extent of angiogenesis in diabetic wounds following odanacatib treatment are evaluated.

Determination of epithelial gap, granulation tissue, vascularization, and collagen content are assessed from tissue samples. Deparaffinized skin-tissue sections are stained with H&E and are analyzed for the epithelial gap (distance between the advancing edges of keratinocyte migration and granulation tissue). Vascularization is detected by staining with CD31 antibody. Collagen content is determined by staining the section with Picro-Sirius, and total ECM content is analyzed by Mason-Goldner trichome staining.

Wound inflammation, proinflammatory cytokine and oxidative stress are also assessed from tissue samples. Wound tissues are homogenized, sonicated, centrifuged and supernatants are subjected to multiplex ELISA for different cytokines (BioRad, Bioplex-Pro). Specifically, the levels of IL-6, TBFβ1, TNF-α, and VEGF are determined. The level of SDF1-α in the tissue homogenates is also determined. The levels of malondialdehyde and the activities of GSH-Px and catalase in the wounds are determined.

Cathepsin K is assessed and mRNA and protein levels of cathepsin K are determined by quantitative RT-PCR and Western analysis respectively. Cathepsin K activity is assessed using a fluorescence-based assay (Abcam). For immunohistochemical detection of cathepsin K, tissue sections are probed with anti-cathepsin K antibody followed by Alexa-Fluor-594 AffiniPure donkey anti-rabbit IgG. Additionally, the levels of cathepsins S and L and matrix metalloproteinases (MMP) 3 and 9 in the wound are assessed. Levels of cystatin and tissue inhibitors of matrix metalloproteinases (TIMPS) in the wounds are also evaluated.

In administering treatment with odanacatib, the composition is applied locally on the wounds or into adjacent dermal tissue, so the systemic exposure is limited and well within the safety margins of the toxicology identified in human studies of the drugs for osteoporosis treatments.

In certain embodiments, the practitioner may periodically monitor or assess the subject for confirmation that no systemic exposure is occurring. If any systemic exposure is detected, the practitioner can then adjust the localized dosage accordingly.

Wound healing is classically divided into hemostasis, inflammation, proliferation, and remodeling. Is can also be described as having an early phase, which begins immediately following skin injury and a cellular phase which involves several types of cells working together to mount an inflammatory response, synthesize granulation tissue, and restore the epithelial layer.

In some embodiments, a wound treatment method comprises administering a cathepsin K inhibition agent at or near the inception of the cellular phase or during the inflammation stage.

Because pathogenesis of diabetic wounds involves multiple physiological factors, a unilateral approach that only tackles cellular growth and migration, as with established growth-promoting treatments such as becaplermin, may be of limited efficacy. A multimodal approach provides options for addressing multiple or alternate physiological targets that impair wound healing. It is beneficial to have treatment options that include modulating protease activity, such as with odanacatib.

Example 13: Wound Treatment Dressings with Cathepsin K Inhibitor

Figure 10:
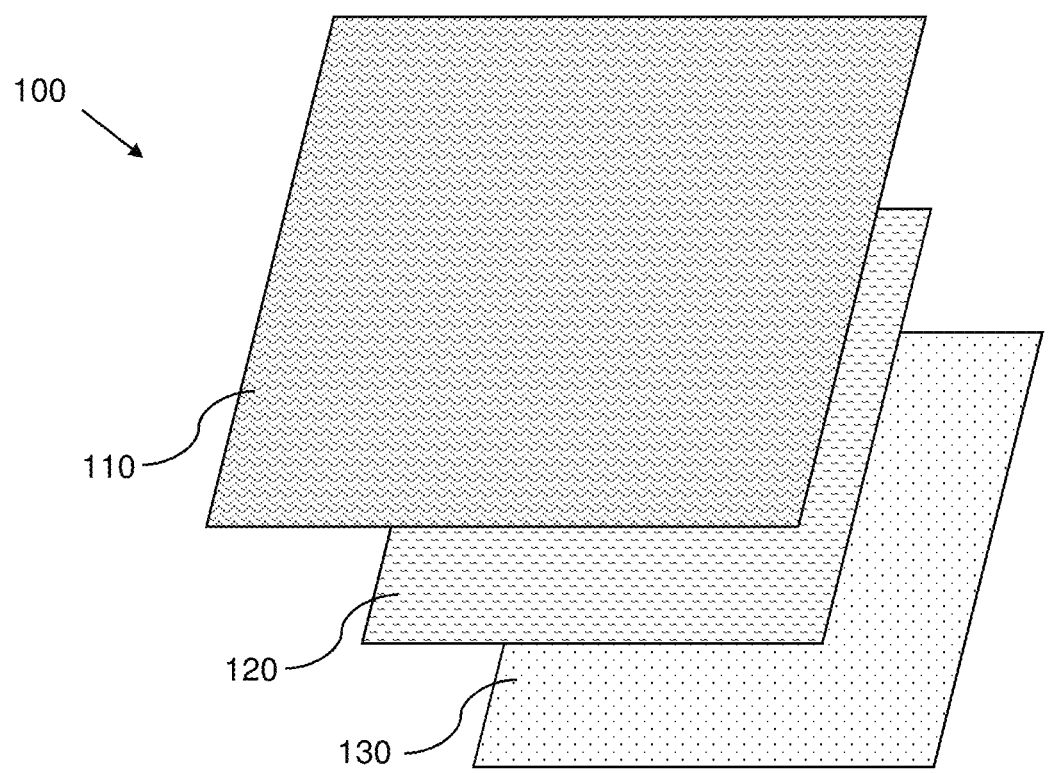
FIG. 10 shows an example of a wound dressing.

FIG. 10 shows a simplified illustration of an example bandage or wound dressing 100. The dressing has a contact layer 130, at least one intermediate layer 120, and an outer layer 110, additional layers may also be present. Each layer 110, 120, 130 may comprise a polymer film, paper, gel, a woven or non-woven fabric, or the like. The contact layer contacts a wound surface. The dressing may include a cathepsin K inhibition agent incorporated into the contact layer and/or in the at least one intermediate layer. The cathepsin K inhibition agent may be released from the layer to the wound over time.

Wound dressings 10 according to embodiments of the invention may be used in any situation in which a general wound dressing might be used, and they may be made in a variety of shapes and sizes to accommodate wounds of various sizes that are situated in various places on the body. However, they may be particularly helpful with complex, difficult, and chronic wounds, like decubitus ulcers, pressure sores, infected wounds, deep and open surgical incisions, and burns. They may be used, for example, after surgical wound debridement, to heal skin burns, and to promote skin graft attachment after surgery.

In particular embodiments, the second layer of a wound dressing can be an elastomeric layer, vapor-permeable film, waterproof film, a woven or nonwoven fabric, mesh, or the like. The composition containing layer and second layer can be bonded using any suitable method (e.g., the application of adhesives, such as pressure sensitive adhesives, hot melt adhesives, curable adhesives; the application of heat or pressure, such as in lamination; a physical attachment through the use of stitching, studs, other fasteners; or the like).

Wound dressings may include adhesives for attachment to the skin or other tissue. Although any adhesive suitable for forming a bond with the skin or other tissue can be used, in certain embodiments a pressure sensitive adhesive is used. Pressure sensitive adhesives are generally defined as adhesives that adhere to a substrate when a light pressure is applied but leave little to no residue when removed. Pressure sensitive adhesives include solvent in solution adhesives, hot melt adhesives, aqueous emulsion adhesives, calenderable adhesives, and radiation curable adhesives.

The most commonly used elastomers in pressure sensitive adhesives can include natural rubbers, styrene-butadiene latexes, polyisobutylene, butyl rubbers, acrylics, and silicones. In particular embodiments, acrylic polymer or silicone-based pressure sensitive adhesives can be used. Acrylic polymers can often have a low level of allergenicity, be cleanly removable from skin, possess a low odor, and exhibit low rates of mechanical and chemical irritation. Medical grade silicone pressure sensitive adhesives can be chosen for their biocompatibility.

Amongst the factors that influence the suitability of a pressure sensitive adhesive for use in wound dressings of particular embodiments is the absence of skin irritating components, sufficient cohesive strength such that the adhesive can be cleanly removed from the skin, ability to accommodate skin movement without excessive mechanical skin irritation, and good resistance to body fluids.

In particular embodiments, the pressure sensitive adhesive can include a butyl acrylate. While butyl acrylate pressure sensitive adhesives can generally be used for many applications, any pressure sensitive adhesive suitable for bonding skin can be used. Such pressure sensitive adhesives are well known in the art.

Other therapeutic compositions can also be incorporated into wound dressings (e.g., bandages, adhesive bandages, transdermal patches). Generally, in these embodiments, compositions are embedded within puffs, gauzes, fleeces, gels, powders, sponges, or other materials that are associated with a second layer to form a wound dressing. Absorption enhancers can also be used to increase the flux of the composition, and particularly the therapeutic protein within the composition, across the skin. The rate of such flux can be controlled by either providing a rate controlling membrane or dispersing the therapeutic protein in a polymer matrix or gel.

The compositions for injection can take such forms as suspensions, solutions or emulsions in oily or aqueous vehicles, and can contain formulatory agents such as suspending, stabilizing, preserving and/or dispersing agents. Injectable formulations include one or more compositions disclosed herein in combination with one or more pharmaceutically acceptable sterile isotonic aqueous or non-aqueous solutions, emulsions, or sterile powders which may be reconstituted into sterile injectable solutions or dispersions just prior to use, which may contain antioxidants, buffers, bacteriostats, or solutes.

Example 14: Methods of Treatment

Methods disclosed herein include treating subjects (humans, veterinary animals (dogs, cats, reptiles, birds, etc.) livestock (horses, cattle, goats, pigs, chickens, etc.) and research animals (monkeys, rats, mice, fish, etc.) with therapeutic proteins disclosed herein including salts and prodrugs thereof. Treating subjects includes delivering therapeutically effective amounts. Therapeutically effective amounts include those that provide effective amounts, prophylactic treatments, and/or therapeutic treatments. Therapeutically effective amounts can be administered to promote wound healing. In particular embodiments, the promotion of wound healing leads to re-epithelialization, reduction in the occurrence and/or severity of ulcers, and/or preservation of nerve function (appropriate signal transduction) and/or integrity (physical state of the nerve).

An "effective amount" is the amount of a therapeutic compound necessary to result in a desired physiological change in the subject. Effective amounts are often administered for research purposes. Effective amounts disclosed herein promote wound healing and/or reduce, control, or eliminate the negative effects of skin damage.

A "prophylactic treatment" includes a treatment administered to a subject who display signs or symptoms of wounds that have not yet become chronic or display only early signs or warning symptoms for the development of chronic wounds or neuropathies such that treatment is administered for the purpose of diminishing, preventing, or decreasing the risk of the wound becoming chronic or developing the chronic wounds or neuropathies further. Thus, a prophylactic treatment functions as a preventative treatment against chronic wounds. A prophylactic treatment also can be administered to subjects at risk for developing chronic wounds before early signs or warning appear.

For example, in subjects at risk for developing chronic wounds, prophylactic treatments can be administered at the time a wound occurs or as soon as is reasonably or practically possible thereafter. Diabetic subjects are one group of subjects at risk for developing chronic wounds. Other subjects at risk for developing chronic wounds include those who suffer from an inflammatory condition.

Non-limiting examples of therapeutic treatment include a treatment administered to a subject who has chronic wounds or neuropathies and is administered to the subject for the purpose of promoting the healing of the chronic wounds. Therapeutic treatments can promote wound healing and/or reduce, control, or eliminate the negative effects of skin damage.

For administration, therapeutically effective amounts (also referred to herein as doses) can be initially estimated based on results from in vitro assays and/or animal model studies. For example, a dose can be formulated in animal models to achieve a circulating concentration range that includes an $IC_{50}$ as determined in cell culture against a particular target. Such information can be used to more accurately determine useful doses in subjects of interest.

The actual dose amount administered to a particular subject can be determined by a physician, veterinarian, or researcher taking into account parameters such as physical and physiological factors including target, body weight, severity of wound, type of wound, previous or concurrent therapeutic interventions, idiopathy of the subject, and route of administration.

The amount and concentration of the composition, as well as the quantity of the pharmaceutical composition administered to a subject, can be selected based on clinically relevant factors, the solubility of the composition, the potency and activity of the composition, and the manner of administration of the composition.

A composition including a therapeutically effective amount, or a pharmaceutically acceptable salt or prodrug thereof, can be administered to a subject for treatment of wounds in a clinically safe and effective manner, including one or more separate administrations of the composition.

For certain indications, the total daily dose of can be about 0.05 ng/mm$^2$ g to about 3.0 ng/mm$^2$ administered to a subject one to three times a day, including administration of total daily doses of about 0.05-3.0, 0.1-3.0, 0.5-3.0, 1.0-3.0, 1.5-3.0, 2.0-3.0, 2.5-3.0, and 0.5-3.0 ng/mm$^2$/wound using 60-minute QD, BID or TID dosing. In one particular example, pharmaceutical compositions can be administered QD or BID to a subject with, e.g., total daily doses of 1.5 ng/mm$^2$/wound 3000 ng/mm$^2$/wound.

Additional useful doses can often range from 0.1 to 5 ng/mm$^2$/wound or from 0.5 to 1 ng/mm$^2$/wound. In other examples, a dose can include 1 ng/mm$^2$/wound, 5 ng/mm$^2$/wound, 10 ng/mm$^2$/wound, 15 ng/mm$^2$/wound, 20 ng/mm$^2$/wound, 25 ng/mm$^2$/wound, 30 ng/mm$^2$/wound, 35 ng/mm$^2$/wound, 40 ng/mm$^2$/wound, 45 ng/mm$^2$/wound, 50 ng/mm$^2$/wound, 55 ng/mm$^2$/wound, 60 ng/mm$^2$/wound, 65 ng/mm$^2$/wound, 70 ng/mm$^2$/wound, 75 ng/mm$^2$/wound, 80 ng/mm$^2$/wound, 85 ng/mm$^2$/wound, 90 ng/mm$^2$/wound, 95 ng/mm$^2$/wound, 100 ng/mm$^2$/wound, etc. up to and including 3,000 ng/mm$^2$/wound or more.

Therapeutically effective amounts can be achieved by administering single or multiple doses during the course of a treatment regimen (e.g., hourly, every 2 hours, every 3 hours, every 4 hours, every 6 hours, every 9 hours, every 12 hours, every 18 hours, daily, every other day, every 3 days, every 4 days, every 5 days, every 6 days, weekly, every 2 weeks, every 3 weeks, or monthly.

Methods of wound treatment may include applying a dressing with an intermediate layer comprising a cathepsin K inhibition agent.

The contact layer may include microneedles.

The contact layer may further include odanacatib.

Example 15: Treatment with Odanacatib Accelerates Wound-Healing in Diabetic Pigs Treatment with odanacatib accelerates wound-healing.

In certain embodiments dosing is 10-250 ng/mm$^2$ of the wound once every three days.

In certain embodiments, formulations and/or injections are formulated for intradermal injections (either in 0.9% saline or liposomal formulation) using an insulin syringe (28 gauge, ½ inch). 200 microliters injected to four corners of the wound and 200 microliters injected to the base of the wound (total volume to be injected 1 mL. The needle is to be insert about ¼ in., with the entire bevel under the skin.

In any of the embodiments, administration can be direct wound infiltration by local injection into the wound margin or instillation into the incision wound, or a combination thereof.

Non-limiting examples of equipment used for intradermal injections is a syringe calibrated in tenths and hundredths of a milliliter, and a ¼ to ½ in., 26 or 27 gauge needle. The angle of administration for an injection can be 5 to 15 degrees.

In other embodiment, microneedle patches are useful for the transport of therapeutic compositions into the skin or across tissue barriers. Transdermal drug delivery provides several advantages over other routes for administering a drug formulation to a patient. Microneedles are short (generally 3 mm or less) needles that can pierce the skin to a depth wherein a substance can be delivered into the epidermis, such that the substance can be readily absorbed by the body. An advantage of the use of microneedles is their ability to penetrate the outermost layers of the skin with only minor discomfort to the patient, as compared to a standard needle.

In certain other embodiments, alternative formulations are topical cream formulated to be applied to the wound twice daily.

Further Examples

According to the embodiments described herein, a wound dressing may be adapted to deliver an agent that degrades cathepsin K, an agent that inhibits the proteolytic action of cathepsin K, or an agent that inhibits the expression of cathepsin K. The agent may include a siRNA and antisense oligonucleotide. The agent may include odanacatib. The dressing may include a bandage, a porous support structure, a biocompatible, biodegradable polymer, a hydrocolloid, a gel matrix, or the like.

According to the embodiments described herein, methods of wound treatment include application of a cathepsin K inhibition agent to an area of damaged skin or external flesh from where skin is injured or missing on a patient. In some embodiments the patient has diabetes mellitus. In some embodiments the patient is pre-diabetic, hypoglycemic, diabetic, or has a metabolic disorder which impairs skin healing.

Wounds include injuries that extend through the epidermis into the dermis. Wounds may include a suture, a surgical incision, a puncture, a surface ulcer that involves full skin thickness, a deep ulcer that penetrates to ligaments or muscle, an ulcer with inflammation of subcutaneous connective tissue, an abscess, a burn, a blister, or a cut.

In some embodiments, a method of treatment comprises administration of odanacatib topically, at a surface without using a physical penetration instrument, such as a needle. It may be applied at a wound-adjacent skin surface, over a wound, or onto inflamed skin near a wound. In some embodiments it is applied to a region within 10 mm, or within 5 mm of break in the epidermis.

In some embodiments, a method of treatment comprises administration of odanacatib by intradermal injection at or near a wound edge. The intradermal injection may comprise administering odanacatib into an epidermal skin layer, into a dermal layer, or into basal regions of a dermal layer. In some embodiments the odanacatib is administered at a dose of 0.1 to 300 ng/mm$^2$ of wound. In some embodiments the odanacatib is administered at a dose of about 3-30 ng/mm$^2$ of wounded skin area. In some embodiments a single dose is administered. In some embodiments, the odanacatib is administered once per day for 5-10 days. In some embodiments, the odanacatib is administered twice per day for 2-20 days. In some embodiments, the odanacatib is administered at least three times in a 10 day period. In some embodiments, the odanacatib is administered at least two times in a 10 day period. In some embodiments an initial dose is administered between the $2^{nd}$ and $10^{th}$ day after a wound injury.

According to the embodiments described herein, a topical agarose matrix-based formulation can be used to deliver cathepsin K siRNA to the diabetic wound. The use of siRNA in treating diabetic wounds has many potential advantages. Using siRNA to target cathepsin K can also be extended to treat related conditions such as pressure ulcers, infections, burns, lower limb ulcers due to venous stasis, and age-related ulcers.

According to the embodiments described herein, a method for treating a wound in a subject in need thereof, comprises administering a therapeutic composition comprising: an agent that degrades cathepsin K, an agent that inhibits the proteolytic action of cathepsin K, or an agent that inhibits the expression of cathepsin K.

In some embodiments, the subject has diabetes. In some embodiments, the subject has a chronic wound.

In some embodiments, the agent is a siRNA.

In some embodiments, the agent is a protease inhibitor.

In some embodiments, the agent is a cathepsin K selective inhibitor.

In some embodiments, the agent is odanacatib.

In particular embodiments, the compositions described herein can be used in conjunction with other wound treatments. For example, in the case of a diabetic ulcer, sharp debridement, pressure relief, and various methods of infection control may be used.

Formulations

In various embodiments, a topical formulation of a composition as described herein can be applied to the wound. In some embodiments, a topical formulation is applied superficially and the wound is then covered by a dressing. In particular embodiments, the dressing is moistened. In some embodiments, the dressing can be moistened by saline. In various embodiments, the dressing can be left in place for up to 6 hours, up to 12 hours, or up to 24 hours. In particular embodiments, the dressing is removed, the topical formulation is reapplied, and a new dressing is used to cover the wound.

In some embodiments, the composition may be applied as a liquid, a gel, a cream, an ointment, a dry adhesive coating, an aerosol, a dry aerosol, a pump spray, a film, a salve, a semi-gel, a foam, a paste, a suspension, an ointment, an emulsion, or a powder.

In some embodiments, the composition may be applied directly to a wound or to a wound-contacting delivery vehicle, such as a suture or wound dressing. A wound dressing may include a bandage, a pad, a medical compress, a medicated sponge, a surgical patch, a hemostatic fleece, a hemostatic pad, a surgical dressing, a wound packing, a swab, or a gauze.

In particular embodiments, the compositions can be in the form of, e.g., gels, ointments, pastes, lotions, creams, sprays, foams, or powders.

A gel is a substantially dilute cross-linked system, which exhibits no flow when in the steady-state. Most gels are liquid, however they behave more like solids due to the three-dimensional cross-linked network within the liquid. Gels can have properties ranging from soft and weak to hard and tough.

An ointment is a homogeneous, viscous, semi-solid preparation, most commonly a greasy, thick oil (oil 80%-water 20%) with a high viscosity. Ointments have a water number, which is the maximum quantity of water that 100 g of a base can contain at 20° C.

A paste includes three agents—oil, water, and powder, one of which includes a therapeutic agent. Pastes can be an ointment in which a powder is suspended.

A lotion also includes oil, water, and powder, but can have additional components (e.g., alcohol to hold the emulsion together) and often has a lower viscosity than a paste.

A cream is an emulsion of oil and water in approximately equal proportions. Creams are thicker than lotions and maintain their shape when removed from a container.

Topical formulations disclosed herein can include components, such as animal and vegetable fats, oils, waxes, paraffins, starch, tragacanth, cellulose derivatives, polyethylene glycols, silicones, bentonites, silicic acid, talc and zinc oxide, or mixtures thereof. In various embodiments, topical formulations may include thickening agents, surfactants, organic solvents, tonicity modifiers, In another embodiment, the composition can be in a unit dosage form, such as in a suitable diluent in sterile, hermetically sealed ampoules or sterile syringes.

In some cases, in order to prolong the effect of a composition, it is desirable to slow the absorption of the composition following injection. Compositions can be formulated as sustained-release systems utilizing semipermeable matrices of solid polymers containing at least one therapeutic protein. Various sustained-release materials have been established and are well known by those of ordinary skill in the art. Sustained-release systems may, depending on their chemical nature, release active ingredients following administration for a few weeks up to over 100 days.

In some embodiments, the composition further comprises one or more anti-inflammatory agent, immunosuppressive agent, immunomodulatory agent, anti-microbial agent, anti-viral agent or a combination thereof.

In some embodiments, the composition further comprises a matrix metalloproteinase (MMP), fibrinogen, thrombin, factor XIII, hydrocolloid, collagen, cellulose, chitosan, zeolite, or calcium.

In some embodiments, the composition is administered topically, intradermally, subcutaneously, intravenously.

In some embodiments, the method further comprises, promoting production of collagen in the ECM.

In some embodiments, the method further comprises, administering a protease inhibitor to the wound or adjacent tissue. In some embodiments, the localized levels of cathepsin K are measured and the composition is applied if localized levels of cathepsin K are elevated. In some embodiments, the localized levels of cathepsin K are measured and the composition is not applied if levels of cathepsin K are not elevated. In some embodiments, measuring localized levels of cathepsin K is performed more than one day after a wound is sustained or a surgery performed. In some embodiments, measuring localized levels of cathepsin K is performed between 1-20 days or between 2-15 days after a surgery.

In some embodiments elevated levels of cathepsin K are higher by 50% or greater than in a tissue sample from a non-diabetic control. In some embodiments elevated levels of cathepsin K are 25%-100% greater in a sample from a wound than in a non-injured tissue sample from the same subject. In some embodiments elevated levels of cathepsin K are identified if cathepsin K mRNA levels measured in a sample from a wound in a subject, as compared with cathepsin K mRNA levels measured in a control sample from a wound from a non-diabetic control, are between 50%-1000% greater in the sample relative to the control. In some embodiments elevated levels of cathepsin K are identified if cathepsin K mRNA levels are more than twice that of a control.

Wound are a type of condition characterized by cell or tissue damage. Wound healing is a dynamic pathway that optimally leads to restoration of tissue integrity and function. The wound healing process consists of three overlapping phases. The first phase is an inflammatory phase, which is characterized by homeostasis, platelet aggregation and degranulation. Platelets as the first response, release multiple growth factors to recruit immune cells, epithelial cells, and endothelial cells. The inflammatory phase typically occurs over days 0-5. The second stage of wound healing is the proliferative phase during which macrophages and granulocytes invade the wound. Infiltrating fibroblasts begin to produce collagen. The principle characteristics of this phase are epithelialization, angiogenesis, granulation tissue formation and collagen production. The proliferative phase typically occurs over days 3-14. The third phase is the remodeling phase where matrix formation occurs. The fibroblasts, epithelial cells, and endothelial cells continue to produce collagen and collagenase as well as matrix metalloproteases (MMPs) for remodeling. Collagen crosslinking takes place and the wound undergoes contraction. The remodeling phase typically occurs from day 7 to one year. Compounds and compositions described herein can be used for promoting wound healing (e.g., promoting or accelerating wound closure and/or wound healing, mitigating scar fibrosis of the tissue of and/or around the wound, inhibiting apoptosis of cells surrounding or proximate to the wound).

Thus, in certain embodiments, there is provided a method for promoting wound healing in a subject, comprising administering to the subject a compound, or pharmaceutically acceptable salt or composition thereof. The method need not achieve complete healing or closure of the wound; it is sufficient for the method to promote any degree of wound closure. In this respect, the method can be employed alone or as an adjunct to other methods for healing wounded tissue. In some embodiments, the composition is applied to a wound exhibiting delayed healing. In some embodiments, the composition is applied to a wound is associated with diabetes mellitus, pressure necrosis, or vasculitis. In some embodiments, the composition is applied to a pressure ulcer, an infection, a burn, a lower limb ulcer associated with venous stasis, an area of neuropathic pain, an arthritic area, or an age-related ulcer.

Methods of Treatment

In some embodiments, a method of treating a wound comprises: delivering a therapeutic composition to a subject in need thereof, wherein the therapeutic composition comprises an agent that degrades cathepsin K, an agent that inhibits the proteolytic action of cathepsin K, or an agent that inhibits the expression of cathepsin K. In some embodiments, the composition is applied to a wound in a diabetic patient undergoing surgery. In some embodiments, the composition is applied to a surgical wound immediately prior to suturing the wound. In some embodiments, the composition is applied to a surgical wound immediately after to suturing the wound. In some embodiments, the composition is applied to a surgical wound in a diabetic patient when applying a wound dressing. In some embodiments, the subject is a diabetic surgical patient, wherein the subject has a medical history of delayed wound healing.

Pharmaceutical Compositions

For administration to an animal or a human, the therapeutic compounds or molecules of the present invention are combined with an acceptable carrier to form a pharmaceutical composition and are administered to the animal or the human. The therapeutic compounds of the present invention may be reconstituted in any pharmaceutically acceptable carrier before use or administration.

Pharmaceutical compositions may be presented in unit dose forms containing a predetermined amount of active ingredient per unit dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions.

Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

Pharmaceutical compositions adapted for injectable administration include aqueous and non-aqueous sterile injection solutions which may contain anti-oxidants, buffers, bacteriostats and solutes; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use.

Extemporaneous injection solutions and suspensions may be prepared from sterile powders, granules and tablets.

A therapeutically effective amount of the agent will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or more usually in a number (such as two, three, four, five or six) of sub-doses per day such that the total daily dose is the same.

The amount of compounds of the present invention that may be combined with the carrier materials to produce a composition in a single dosage form will vary depending upon the host treated, the particular mode of administration.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms Combinations of Therapies The compounds of Formula (I) and pharmaceutically acceptable salts thereof may be employed alone or in combination with other therapeutic agents. The compounds and pharmaceutically acceptable salts thereof and the other pharmaceutically active agent(s) may be administered together or separately and, when administered separately, administration may occur simultaneously or sequentially, in any order, by any convenient route in separate or combined pharmaceutical compositions.

The amounts of the compound(s) or pharmaceutically acceptable salt(s) thereof and the other pharmaceutically active agent(s) and the relative timings of administration will be selected in order to achieve the desired combined therapeutic effect. The compounds and further therapeutic agent(s) may be employed in combination by administration simultaneously in a unitary pharmaceutical composition including both compounds. Alternatively, the combination may be administered separately in separate pharmaceutical compositions, each including one of the compounds in a sequential manner wherein, for example, the compound of the invention is administered first and the other second and vice versa. Such sequential administration may be close in time (e.g. simultaneously) or remote in time. Furthermore, it does not matter if the compounds are administered in the same dosage form, e.g. one compound may be administered topically and the other compound may be administered orally.

Combination Therapies

In some embodiments, a compound described herein is administered together with an additional "second" therapeutic agent or treatment. The choice of second therapeutic agent may be made from any agent that is typically used in a monotherapy to treat the indicated disease or condition. As used herein, the term "administered together" and related terms refers to the simultaneous or sequential administration of therapeutic agents in accordance with this invention. For example, a compound may be administered with another therapeutic agent simultaneously or sequentially in separate unit dosage forms or together in a single unit dosage form.

In one embodiment, where a second therapeutic agent is administered to a subject, the effective amount of the compound is less than its effective amount would be where the second therapeutic agent is not administered. In another embodiment, the effective amount of the second therapeutic agent is less than its effective amount would be where the compound is not administered. In this way, undesired side effects associated with high doses of either agent may be minimized. Other potential advantages (including without limitation improved dosing regimens and/or reduced drug cost) will be apparent to those of skill in the art. The additional agents may be administered separately, as part of a multiple dose regimen, from the compounds described herein. Alternatively, those agents may be part of a single dosage form, mixed together with the compounds in a single composition.

Kits

The combinations may be presented as a combination kit. By the term "combination kit" "or kit of parts" as used herein is meant the pharmaceutical composition or compositions that are used to administer the combination. When both compounds are administered simultaneously, the combination kit can contain both compounds in a single pharmaceutical composition, such as an ampoule, or in separate pharmaceutical compositions. When the compounds are not administered simultaneously, the combination kit will contain each compound in separate pharmaceutical compositions either in a single package or in separate pharmaceutical compositions in separate packages.

The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

When the combination is administered separately in a sequential manner wherein one is administered first and the other second or vice versa, such sequential administration may be close in time or remote in time. For example, administration of the other agent several minutes to several dozen minutes after the administration of the first agent, and administration of the other agent several hours to several days after the administration of the first agent are included, wherein the lapse of time is not limited. For example, one agent may be administered once a day, and the other agent may be administered 2 or 3 times a day, or one agent may be administered once a week, and the other agent may be administered once a day and the like.

When combined in the same composition it will be appreciated that the two compounds must be stable and compatible with each other and the other components of the composition and may be formulated for administration. When formulated separately they may be provided in any convenient composition, conveniently, in such a manner as known for such compounds in the art.

When the compound is used in combination with a second therapeutic agent active against the same disease, condition or disorder, the dose of each compound may differ from that when the compound is used alone. Appropriate doses will be readily appreciated by those skilled in the art.

In one embodiment the mammal in the methods and uses of the present invention is a human.

Pharmaceutically Acceptable Carriers

In general, the nature of the carrier will depend on the particular mode of administration being employed. For instance, carrier formulations may include pharmaceutically and physiologically acceptable fluids such as water, physiological saline, balanced salt solutions, aqueous dextrose, glycerol or the like as a vehicle. The composition may include gelling agents, emulsifying agents and the like. In addition to biologically-neutral carriers, pharmaceutical compositions to be administered can contain minor amounts of non-toxic auxiliary substances, such as wetting or emulsifying agents, preservatives, suspending agents, thickening agents, anti-oxidants, buffers, bacteriostats, and pH buffering agents and the like, for example sodium acetate or sorbitan monolaurate. In yet another embodiment, the pharmaceutical compositions can be delivered in a controlled release system. Combinations of administration methods may also be employed.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The pharmaceutical compositions provided herein, including those for use in treating disorders, for example skin disorders, may be administered locally to a wound and adjacent area by administration routes, such as subcutaneous, intradermal, and topical. They may be administered in different forms, including but not limited to solutions, emulsions and suspensions, microspheres, particles, microparticles, nanoparticles, and liposomes. In one embodiment, therapeutic compounds are combined with an acceptable carrier to form a pharmaceutical composition for topical administration to a wound site.

The amount of the pharmaceutical compositions that will be effective depends on the nature of the disorder or condition to be treated, as well as the stage of the disorder or condition. Effective amounts can be determined by standard clinical techniques. The precise dose to be employed in the formulation should be decided according to the judgment of the health care practitioner and each subject's circumstances.

The pharmaceutical compositions of the present disclosure can be administered in a single dose application, at about the same dose throughout a treatment period, in an escalating dose regimen, or the dose may be varied during the course of a treatment based on the condition of the subject being treated, the severity of the disease or condition, the apparent response to the therapy, and/or other factors as judged by one of ordinary skill in the art.

The terminology used herein is for the purpose of describing particular example embodiments only and is not intended to be limiting. It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. As used herein, the singular forms "a," "an," and "the" may include plural forms, unless the context clearly indicates otherwise. The terms "comprises," "comprising," "including," and "having," are inclusive and specify the presence of stated features, integers, steps, operations, elements, and/or components, but do not preclude the presence or addition of one or more other features, integers, steps, operations, elements, components, and/or groups. The method steps, processes, and operations described are not to be construed as necessarily requiring their performance in the particular order discussed or illustrated, unless specifically identified as an order of performance. It is also to be understood that additional or alternative steps may be employed. Individual elements or features of a particular embodiment are generally not limited to that particular embodiment, but, where applicable, are interchangeable and can be used in a selected embodiment, even if not specifically shown or described.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for treating a skin wound comprising:
  administering to the skin wound a therapeutic composition comprising an agent that degrades or inhibits cathepsin K;
  wherein the agent comprises at least one of odanacatib, cathepsin K inhibitor II, or an siRNA that has a sequence that is complementary to a nucleic acid sequence encoding cathepsin K; and,
  wherein the agent is intradermally administered in dosages ranging from 0.3 ng to 3000 ng per $mm^2$ wound.

2. The method of claim 1, wherein the agent is intradermally administered in dosages ranging from 30 ng to 300 ng per $mm^2$ wound.

3. The method of claim 1, wherein the agent is intradermally administered in dosages ranging from 10 ng to 250 ng per $mm^2$ wound at a dosing frequency ranging from three times per day to once every three days.

4. The method of claim 1, wherein the agent is administered in a time-dependent regime, with an initial small dose, a subsequent large dose, and one or more following small doses, wherein the large dose provides the agent in a range of 1.5 to 100 times greater than provided in the small dose.

5. The method of claim 1, wherein the agent is initially administered 2 to 10 days after initial wounding.

6. The method of claim 1, wherein the agent comprises odanacatib.

7. The method of claim 1, wherein the agent is intradermally administered at prescribed intervals of 0, 3, 7, 14 and 21 days after initial wounding.

8. The method of claim 1, wherein the therapeutic composition is first administered at least 3 days after initial wounding.

9. The method of claim 1, wherein the skin wound is on a lower limb of a diabetic subject.

10. The method of claim 1, wherein the skin wound is a chronic wound.

11. A topical formulation for treating a cutaneous wound comprising:
  a therapeutic composition comprising becaplermin and at least one of: odanacatib, cathepsin K inhibitor II, or an siRNA that has a sequence that is complementary to a nucleic acid sequence encoding cathepsin K; and
  a carrier, wherein:
    the carrier is provided as one of: a gel, an ointment, a paste, a lotion, a cream, a liquid, a spray, a foam, or a powder,
    the topical formulation is a mixture, suspension, solution, or emulsion, of the therapeutic composition with the carrier, and
    the topical formulation is configured to be applied to a skin surface without using physical penetration.

12. The topical formulation of claim 11, wherein the therapeutic composition is provided in a medical compress, a medicated sponge, a surgical patch, a dry adhesive coating, an aerosol, a dry aerosol, a pump spray, a film, a hemostatic fleece, a hemostatic pad, a gauze, a salve, a semi-gel, a gel, a foam, a paste, a suspension, an ointment, an emulsion, a moldable form, a surgical dressing, a wound packing, or a swab.

13. The topical formulation of claim 11, wherein the therapeutic composition comprises odanacatib.

14. The topical formulation of claim 11, wherein the topical formulation further comprises one or more of: an anti-inflammatory agent, an immunosuppressive agent, an immunomodulatory agent, an anti-microbial agent, an anti-viral agent, a matrix metalloproteinase (MMP), fibrinogen, thrombin, factor XIII, hydrocolloid, collagen, cellulose, chitosan, zeolite, or calcium.

15. The topical formulation of claim 11, wherein the therapeutic composition is provided in a wound dressing comprising:
  a contact layer,
  an intermediate layer comprising a porous support structure, and
  an outer layer,
    wherein the therapeutic composition is incorporated into at least one of the contact layer or the intermediate layer.

16. A method for treating a skin wound comprising:
  administering to the skin wound a therapeutic composition comprising an agent that degrades or inhibits cathepsin K;
  wherein the agent comprises at least one of: odanacatib, cathepsin K inhibitor II, or an siRNA that has a sequence that is complementary to a nucleic acid sequence encoding cathepsin K; and,
  wherein the agent is administered in a time-dependent regime, with an initial small dose, a subsequent large dose, and one or more following small doses, wherein the large dose provides the agent in a range of 1.5 to 100 times greater than provided in the small dose.

17. The method of claim 16, wherein the agent comprises odanacatib.

18. The method of claim 16, wherein the therapeutic composition is administered topically to the skin wound.

19. The method of claim 16, wherein the therapeutic composition comprises an agarose matrix-based media.

20. The method of claim 16, wherein the therapeutic composition is provided in at least one of: a medical compress, a medicated sponge, a surgical patch, a dry adhesive coating, an aerosol, a dry aerosol, a pump spray, a film, a hemostatic fleece, a hemostatic pad, a gauze, a salve, a semi-gel, a gel, a foam, a paste, a suspension, an ointment, an emulsion, a moldable form, a surgical dressing, a wound packing, or a swab.

21. The method of claim 16, wherein the therapeutic composition further comprises becaplermin.

22. The method of claim 16, wherein the therapeutic composition further comprises at least one of: an anti-inflammatory agent, an immunosuppressive agent, an immunomodulatory agent, an anti-microbial agent, an anti-viral agent, fibrinogen, thrombin, factor XIII, hydrocolloid, collagen, cellulose, chitosan, zeolite, calcium, or a matrix metalloproteinase (MMP).

23. The method of claim 16, wherein administering the therapeutic composition to the skin wound comprises: applying the therapeutic composition to a wound-adjacent skin surface, wherein the wound-adjacent skin surface is a region within 10 mm of a break in the epidermis.

24. The method of claim 16, wherein the therapeutic composition is first administered at least 3 days after initial wounding.

25. The method of claim 16, wherein the agent is initially administered 2 to 7 days after initial wounding.

26. The method of claim 16, wherein the skin wound is on a lower limb of a diabetic subject.

27. The method of claim 16, wherein the skin wound is a chronic wound.

28. A method for treating a skin wound comprising:
administering to the skin wound a therapeutic composition comprising an agent that degrades or inhibits cathepsin K;
wherein the agent comprises at least one of odanacatib, cathepsin K inhibitor II, or an siRNA that has a sequence that is complementary to a nucleic acid sequence encoding cathepsin K; and,
wherein the agent is intradermally administered at prescribed intervals of 2 to 7 days after initial wounding.

29. The method of claim 28, wherein the agent comprises odanacatib.

30. A method for treating a skin wound in a diabetic subject, comprising:
topically administering to the skin wound a topical formulation comprising:
an agent that degrades or inhibits cathepsin K, wherein the agent comprises odanacatib; and
a carrier provided as one of: a gel, an ointment, a paste, a lotion, a cream, a liquid, a spray, a foam, or a powder; wherein:
the topical formulation is a mixture, suspension, solution, or emulsion, of the agent with the carrier.

31. The method of claim 30, wherein the carrier comprises a liquid.

32. The method of claim 30, wherein the topical formulation further comprises becaplermin.

33. The method of claim 30, wherein the carrier comprises a gel.

34. The method of claim 30, wherein the skin wound comprises a skin injury that extends through the epidermis into the dermis.

* * * * *